US007074779B2

(12) United States Patent
Sui et al.

(10) Patent No.: US 7,074,779 B2
(45) Date of Patent: Jul. 11, 2006

(54) ESTRIENO[3,2-B]/[3,4-C]PYRROLE DERIVATIVES USEFUL AS MODULATORS OF THE ESTROGEN RECEPTORS

(75) Inventors: Zhihua Sui, Flemington, NJ (US); Xuqing Zhang, Montgomery Township, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 305 days.

(21) Appl. No.: 10/612,138

(22) Filed: Jul. 2, 2003

(65) Prior Publication Data

US 2005/0004090 A1 Jan. 6, 2005

(51) Int. Cl.
*A61K 31/58* (2006.01)
*C07J 71/00* (2006.01)

(52) U.S. Cl. ........................................ 514/176; 540/49

(58) Field of Classification Search .................. 540/49; 514/176

See application file for complete search history.

(56) References Cited

U.S. PATENT DOCUMENTS

| | | | |
|---|---|---|---|
| 5,726,186 | A | 3/1998 | Grese |
| 6,004,971 | A | 12/1999 | Grese |
| 6,133,288 | A | 10/2000 | Grese |
| 6,262,270 | B1 | 7/2001 | Draper et al. |

FOREIGN PATENT DOCUMENTS

| | | |
|---|---|---|
| EP | 0761669 | 11/2000 |
| WO | WO 97/09044 | 3/1997 |
| WO | WO 01/01969 | 1/2001 |

OTHER PUBLICATIONS

Clinton, R.O. et al.: "Communications to the Editor. Steroidal [2,3-d]isoxezoles". Journal of Organic Chemistry, Jan. (1961), 26, p. 279. Sterling-Winthrop Research Institute, New York.
Ackerman, J.H. et al.: "Steroidal Heterocycles. X. Sterodial[3,2d]pyrimidines and Related Compounds". Sterling-Winthrop Research Institute, New York, Journal of Medical Chemistry, vol. 7, (1964), pp. 238-240.
Albert, J.L. et al.: "Estrogen Regulation of Placental Alkaline Phosphatase Gene Expression in a Human Endometrial Adenocarcinoma Cell Line". Cancer Research, (50), pp. 3306-3310, Jun. 1, 1990.
Allan, G.F. et al.: "An Ultrahigh-Throughput Screening Assay for Estrogen Receptor Ligands". Analytical Biochemistry vol. 275, pp. 243-247, (1999).
Clinton, R.O. et al.: "Steroidal[3,2-c]pyrazoles. II. Androstanes, 19-Norandrostanes and their Unsaturated Analogs". Journal of American Chemical Society, (1961), 83, pp. 1478-1491. Sterling Winthrop Research Institute, New York.
Gupta, R. et al.: "Synthesis and Biological Activity of Azasteroidal [3,2-c] and [17, 16-c]pyrazoles". European Journal of Medical Chemistry, (1996), 31, pp. 241-247.
Hirschmann, R. et al.: "Synthesis and Structure of Steroidal Pregn-4-eno-and 5 a-Pregano [3,2-c]pyrazoles. A Novel class of Potent Anti-Inflammatory Steroids". Journal of American Chemical Society, (1964), 86, pp. 1520-1527.
Laitonjam, W.S. et al.: "Synthesis of some A- and D-ring Fused Steroidal Pyrazoles, Isoxazoles and Pyrimidines". Steroids (2002), 67, pp. 203-209.
Manson, A.J. et al.: "Steroidal Heterocycles. VII. Androstano[2,3-d]isozazoles and Related Compounds" Journal of Medicinal Chemistry (1963) 8, No. 1, pp. 1-9.
Radu, I. et al.: "New Efficient Pathway for the Synthesis of 3-Aminoestrone", Tetrahedron Letters (2002), 43, pp. 7617-7619.
Rottlander, M. et al.: "Palladium-Catalyzed Cross-Coupling Reactions with Aryl Nonaflates: A Practical Alternative to Aryl Triflates" (1998), 63, pp. 203-208.
Weidner, J.J. et al: "Preparation of N-Aryl-2-hydroxypropionamides from Hydroxy Aromatic Compounds Using a One-Pot Smiles Rearrangement Procedure." Tetrahedron, (1997), 53, No. 18, pp. 8303-8312.
Welshons, W.V.: "Stimulation of breast cancer cells in vitro by the environmental enterolactone and the phytoestrogen equol". Breast Cancer Research and Treatment 10, (1987), pp. 169-175.

*Primary Examiner*—Barbara P. Badio

(57) ABSTRACT

The present invention is directed to novel estrieno[3,2-b]/[3,4-c]pyrrole derivatives, pharmaceutical compositions containing them and their use in the treatment of disorders and diseases mediated by an estrogen receptor.

17 Claims, No Drawings

ESTRIENO[3,2-B]/[3,4-C]PYRROLE DERIVATIVES USEFUL AS MODULATORS OF THE ESTROGEN RECEPTORS

FIELD OF THE INVENTION

The present invention is directed to novel estrieno[3,2-b]/[3,4-c]pyrrole derivatives, pharmaceutical compositions containing them and their use in the treatment or prevention of disorders and diseases mediated by an estrogen receptor such as hot flashes, vaginal dryness, osteopenia, osteoporosis, hyperlipidemia, loss of cognitive function, degenerative brain diseases, cardiovascular diseases, cerebrovascular diseases, hormone sensitive cancers and hyperplasia (in tissues including breast, endometrium, and cervix in women and prostate in men), endometriosis, uterine fibroids, osteoarthritis; and as contraceptive agents either alone or in combination with a progestogen or progestogen antagonist. The compounds of the invention are selective estrogen receptor modulators.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in women's body.

Endogenous estrogens, such as 17b-estradiol and estrone, play a central role in the development of and maintenance of the female sex organs, mammary glands, and other sexual characteristics. In addition to their role as female sex hormone, estrogens are involved in the growth and function of a number of other tissues, such as the cardiovascular system, the central nervous system, and the skeleton, both in females and males. The significance of the estrogens in the development of the female reproductive system led to the development of a variety of compounds that interact with the estrogen receptors, such as contraceptives and agents for treatment of breast cancers. More recently, intensive efforts have focused on the selective estrogen receptor modulators for treatment and prevention of postmenopausal conditions, such as osteoporosis, coronary artery disease, depression and Alzheimer disease.

Menopause is defined as the permanent cessation of menses due to loss of ovarian follicular function and the almost termination of estrogen production. The midlife transition of menopause is characterized by a decrease in estrogen that provokes both short-term and long-term symptoms with the vasomotor, urogenital, cardiovascular, skeletal and central nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy and stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left untreated, the problems can become permanent.

Heart attack and stroke are major causes of morbility and mortality among senior women. Female morbility from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure and a decrease of bone strength. Rapid loss of bone mass during the year immediately following menopause leads to postmenopausal osteoporosis and increased risk of fracture.

Estrogen deficiency is also one of the causes for the degenerative changes in the central nervous system and may lead to Alzheimer's disease and decline of cognition. Recent evidence suggests an association between estrogen, menopause and cognition. More particularly, it has been reported that estrogen replacement therapy and the use of estrogen in women may prevent the development of AD and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown significant benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to age of 75 years.

However, there are numerous undesirable effects associated with ERT that reduce patient compliance. Venous thromboembolism, gallbladder disease, resumption of menses, mastodynia and a possible increased risk of developing uterine and/or breast cancer are the risks associated with ERT. Up to 30% of women who were prescribed ERT did not fill the prescription, and the discontinuation rate is between 38% and 70%, with safety concerns and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for arteriosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

SUMMARY OF THE INVENTION

The present invention is directed to a compound of formula (I) or (II)

(I)

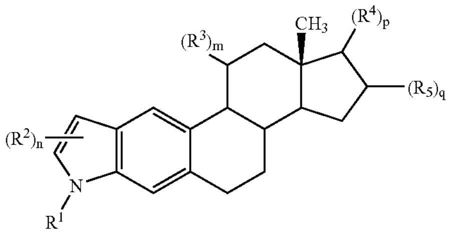

or (II)

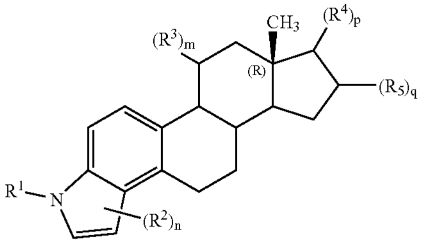

wherein $R^1$ is selected from the group consisting of hydrogen, hydroxy, A, —O-A, C(O)-A and —$SO_2$-A;

n is an integer from 0 to 2;

each $R^2$ is independently selected from the group consisting of hydroxy, carboxy, halogen, -A, —O-A, —C(O)-A, —C(O)O-A, amino, alkylamino, dialkylamino, cyano, aminocarbonyl, alkylaminocarbonyl, dialkylaminocarbonyl, —SH, —S-A, —SO-A, —$SO_2$-A, —$SO_2$—$NH_2$, —$SO_2$—NH(alkyl) and —$SO_2$—N(alkyl)$_2$;

m is an integer from 0 to 2;

each $R^3$ is independently selected from the group consisting of -A, —O-A, —S-A, —NH-A, —N(A)$_2$ and —C(O)-A;

p is an integer from 1 to 2;

each $R^4$ is independently selected from the group consisting of hydroxy, carboxy, cyano, -A, alkenyl, -alkenyl-A, alkynyl, -alkynyl-A, —O-A, —$NH_2$, NH(A), —N(A)$_2$, —N(A)-C(O)-A, —NH—C(O)-A, —C(O)—N(A)$_2$, —C(O)—$NH_2$, —C(O)—NH-A, —$SO_2$—N(A)$_2$, —$SO_2$—NH(A), —$SO_2$—$NH_2$, —N(A)-$SO_2$-A, —NH—$SO_2$-A, —C(O)O-A, —OC(O)H and —OC(O)-A;

alternatively, when p is 2, two $R^4$ groups may be taken together as oxo or ═N(OH);

q is an integer from 0 to 2;

each $R^5$ is independently selected from the group consisting of hydroxy, carboxy; halogen, alkyl, alkoxy, cycloalkyl and —C(O)-A; wherein the alkyl group is optionally substituted with one or more substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one or more substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more estrogen receptors in a subject in need thereof comprising administering to the subject a therapeutically effective amount of any of the compounds or pharmaceutical compositions described above.

Illustrating the invention is a method of contraception comprising administering to a subject in need thereof cotherapy with a therapeutically effective amount of any of the compounds described herein with a progestogen or progestogen antagonist.

Another example of the invention is the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) a degenerative brain disorder, (h) a cardiovascular disease, (i) a cerebrovascular disease (j) breast cancer, (k) endometrial cancer, (l) cervical cancer, (m) prostate cancer, (n) benign prostatic hyperplasia, (o) endometriosis, (p) uterine fibroids, (q) osteoarthritis and for (r) contraception in a subject in need thereof.

DETAILED DESCRIPTION OF THE INVENTION

The present invention is directed to compounds of formula (I) or (II)

(I)

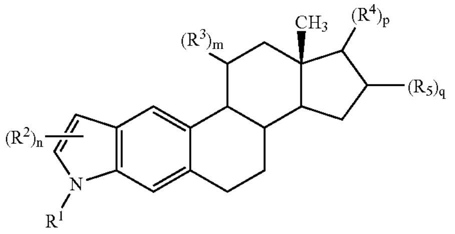

or (II)

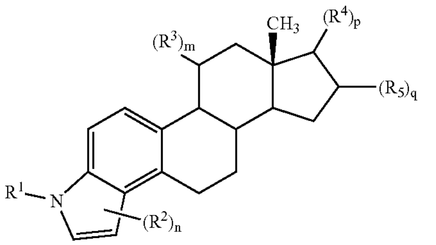

wherein $R^1$, n, $R^2$, m, $R^3$, p, $R^4$, q and $R^5$ are as herein defined. The compounds of the present invention are modulators of an estrogen receptor, useful for the treatment and prevention of disorders associated with estrogen depletion, including, but not limited to hot flashes, vaginal dryness, osteopenia, osteoporosis, hyperlipidemia, loss of cognitive function, degenerative brain diseases, cardiovascular diseases and cerebrovascular diseases; for the treatment of hormone sensitive cancers and hyperplasia (in tissues including breast, endometrium, and cervix in women and prostate in men); for the treatment and prevention of endometriosis, uterine fibroids, and osteoarthritis; and as contraceptive agents either alone or in combination with a progestogen or progestogen antagonist.

In an embodiment of the present invention is a compound of formula (I). In another embodiment of the present invention is a compound of formula (II).

In another embodiment of the present invention $R^1$ is selected from the group consisting of hydrogen, hydroxy, alkyl, aryl, aralkyl, —O-alkyl, —O-aryl, —O-aralkyl, C(O)-A and —$SO_2$-A. In another embodiment of the present invention $R^1$ is selected from the group consisting of hydrogen and —$SO_2$-A. Preferably, $R^1$ is selected from the group consisting of hydrogen and —$SO_2$-alkyl, more preferably $R^1$ is hydrogen or methylsulfonyl.

In an embodiment of the present invention A is selected from the group consisting of alkyl, aryl and aralkyl; wherein the alkyl, aryl or aralkyl group is optionally substituted with one or more, preferably one to three, more preferably on to two substituents independently selected from halogen, hydroxy, carboxy, lower alkyl, lower alkoxy, nitro, cyano, amino, lower alkylamino, or di(lower alkyl)amino.

In an embodiment of the present invention n is an integer from 0 to 1, preferably n is 0. In an embodiment of the present invention $R^2$ is selected from the group consisting of carboxy, halogen, -A, —C(O)-A, —C(O)O-A, cyano, —S-A, —SO-A, —$SO_2$-A, —$SO_2$—$NH_2$, —$SO_2$—NH (alkyl) and —$SO_2$—N(alkyl)$_2$. Preferably $R^2$ is selected from the group consisting of —S-A, more preferably $R^2$ is selected from the group consisting of —S-(alkyl), more preferably still, $R^2$ is methylthio.

In an embodiment of the present invention m is an integer from 0 to 1, preferably m is 0.

In an embodiment of the present invention $R^3$ is selected from the group consisting of -A, —O-A, —S-A, —NH-A and —C(O)-A.

In an embodiment of the present invention p is to 1. In an embodiment of the present invention $R^4$ is selected from the group consisting of hydroxy and —O—C(O)-A. Preferably, $R^4$ is selected from the group consisting of hydroxy, —O—C (O)-(alkyl), —O—C(O)-(alkyl)-$CO_2H$ and alkynyl. More preferably, $R^4$ is selected from the group consisting of hydroxy, n-butylcarbonyloxy, 1-carboxy-n-butylcabonyloxy and ethynyl.

In an embodiment of the present invention p is 2 and two $R^4$ groups are taken together as oxo or =N(OH). Preferably, p is 2 and two $R^4$ groups are taken together as oxo.

In an embodiment of the present invention $R^4$ is selected from the group consisting of hydroxy, —$NH_2$, —NH(A), —NH(A), —C(O)$NH_2$, —C(O)—NH(A), —$SO_2$—$NH_2$, —$SO_2$—NH(A) and —OC(O)-A, and the $R^4$ group is in a β-orientation. In another embodiment of the present invention $R^4$ is selected from the group consisting of hydroxy, carboxy, cyano, -A, alkenyl, -alkenyl-A, alkynyl, -alkynyl-A, —O-A, —$NH_2$, —NH(A), —N(A)$_2$, —N(A)-C(O)-A, —NH—C(O)-A, —C(O)—N(A)$_2$, —C(O)—$NH_2$, —C(O)—NH-A, —$SO_2$—N(A)$_2$, —$SO_2$—NH(A), —$SO_2$—$NH_2$, —N(A)-$SO_2$-A, —NH—$SO_2$-A, —C(O)O-A, —OC(O)H and —OC(O)-A and the $R^4$ group is in an α-orientation. In another embodiment of the present invention $R^4$ is selected from the group consisting of hydrox, carboxy, cyano, lower alkyl, lower alkenyl and lower alkynyl and is in the α-orientation. In yet another embodiment of the present invention, two $R^4$ groups are taken together as oxo or =N(OH).

In an embodiment of the present invention, q is an integer from 0 to 1, preferably q is 0.

In an embodiment of the present invention $R^5$ is selected from the group consisting of carboxy, halogen, lower alkyl, and —C(O)-A. Preferably $R^5$ is hydrogen.

Representative compounds of the formula (I) and (II) of the present invention are as listed in Table 1 and 2.

TABLE 1

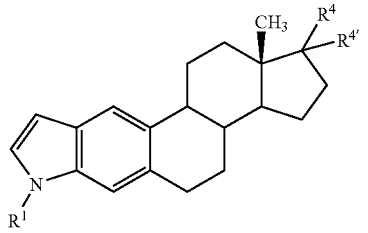

| ID No. | $R^1$ | $R^4$ | $R^{4'}$ |
|---|---|---|---|
| 1 | methylsulfonyl | oxo | — |
| 3 | H | oxo | — |
| 7 | methylsulfonyl | β-hydroxy | H |
| 8 | H | β-hydroxy | H |
| 10 | H | β-hydroxy | α-ethynyl |
| 12 | H | β-[-OC(O)-n-butyl] | H |
| 13 | H | β-[OC(O)-n-butyl-COOH] | H |
| 14 | H | β-[-OC(O)-n-butyl-$COO^-Na^+$] | H |

TABLE 2

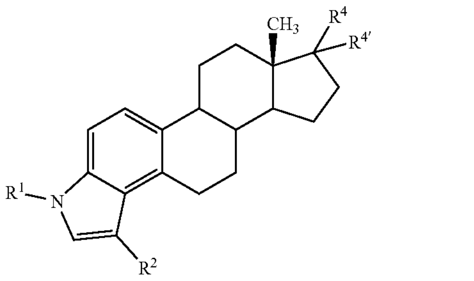

| ID No. | $R^1$ | $R^2$ | $R^4$ | $R^{4'}$ |
|---|---|---|---|---|
| 2 | methylsulfonyl | H | oxo | — |
| 4 | H | H | oxo | — |
| 5 | methylsulfonyl | H | oxo | — |
| 6 | H | H | β-hydroxy | H |
| 9 | H | H | β-hydroxy | α-ethynyl |
| 11 | H | H | β-[-OC(O)-n-butyl] | H |
| 15 | H | metylthio | oxo | — |

As used herein, unless otherwise noted, the term "halogen" shall mean chlorine, bromine, fluorine and iodine.

As used herein, unless otherwise noted, the term "alkyl" whether used alone or as part of a substituent group, include straight and branched carbon chains. For example, alkyl groups include methyl, ethyl, propyl, isopropyl, butyl, isobutyl, sec-butyl, t-butyl, pentyl and the like. Preferably, the alkyl group contains one to eight carbon atoms. Unless otherwise noted, "lower" when used with alkyl means a carbon chain composition of one to four carbon atoms.

As used herein, unless otherwise noted, the term "alkenyl" whether used alone or as part of a substituent group, shall include straight and branched chains containing at least one unsaturated double bond. For example, vinyl, propenyl or allyl, butenyl, buten-2-yl, buten-3-yl, 2-methyl-buten-2-yl, and the like. Preferably, the alkenyl group contains two to eight carbon atoms. Unless otherwise noted, "lower" when used with alkenyl means a carbon chain composition of two to four carbon atoms containing at least one unsaturated double bond.

As used herein, unless otherwise noted, the term "alkynyl" whether used alone or as part of a substituent group, shall include straight and branched chains containing at least one unsaturated triple bond. For example, ethynyl, propynyl, butyn-2-yl, and the like. Preferably, the alkynyl group contains two to eight carbon atoms. Unless otherwise noted, "lower" when used with alkynyl means a carbon chain composition of two to four carbon atoms containing at least one unsaturated triple bond.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to a carbocylic aromatic group such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "cycloalkyl" shall mean any stable three to eight, preferably five to eight, more preferably five to six membered monocyclic, saturated ring system, for example cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, the notation "*" shall denote the presence of a stereogenic center.

When a particular group is "substituted" (e.g., aryl, aralkyl, cycloalkyl, heterocycloalkyl, heteroaryl), that group may have one or more substituents, preferably from one to five substituents, more preferably from one to three substituents, more preferably still from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylalkylaminocarbonylalkyl" substituent refers to a group of the formula

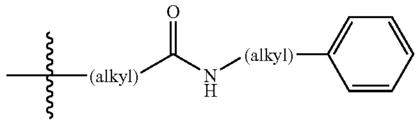

Unless other wise note, the position of substituents on the core structures of the compounds of formula (I) and (II) shall be denoted based on the following numbering system.

The position of substituent(s) on a compound of formula (I) shall be numbered such that the core of rings A, B, C and D are numbered based on accepted convention, and the fifth E ring positions are denoted with lower case letters a, b and c, beginning from the N atom, as follows:

(I)

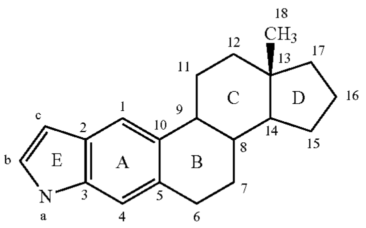

The position of substituent(s) on a compound of formula (II) shall be similarly denoted, as follows:

(II)

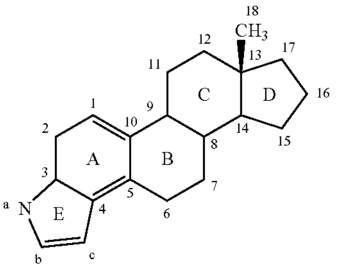

For the compounds of the present invention, each $R^4$ substituent may be in an α- or a β-orientation, wherein in the α- orientation the $R^4$ group is below the plane of the core molecule and in the β-orientation the $R^4$ group is above the plane of the core molecule.

Abbreviations used in the specification, particularly the Schemes and Examples, are as follows:

Ac=Acetyl
AcOH=Acetic acid
BINAP=2,2'-bis(diphenylphosphino)-1,1'-binaphthyl
BnOH=Benzyl alcohol
$Bu_3N$=Tributyl amine
DCC=N,N'-Dicyclohexylcarbodiimide
DCM=Dichloromethane
DIC=N,N'-Diisopropylcarbodiimide
DIPEA=Diisopropylethylamine
DMAP=4-N,N-Dimethylaminopyridine
DMF=N,N-Dimethylformamide
DMSO=Dimethylsulfoxide
DPPE=1,2-Bis(diphenylphosphino)-ethane
DPPP=1,3-Bis(diphenylphosphino)-propane
$Et_2O$=Diethyl ether
EtOAc=Ethyl acetate
EtOH=Ethanol
HEPES=4-(2-Hydroxyethyl)-1-piperazine ethane sulfonic acid
LDA=Lithium diisopropylamine
LHMDS or LiHMDS=Lithium bis(trimethylsilyl)amide
mCPBA=meta-chloroperoxybenzoic acid
Me=Methyl (i.e. —$CH_3$)
MeOH=Methanol
NaO-t-Bu=Sodium t-butoxide
NBS=N-bromosuccinimide
NIS=N-idoosuccinimide
NMO=N-methylmorpholine oxide
PBS=Phosphate buffered saline
$Pd(OAc)_2$=Palladium (II) acetate
$Pd_2(dba)_3$=Tris(dibenzylideneacetone) dipalladium (0)
$Pd(PPh_3)_2Cl_2$=Dichlorobis(triphenyphosphine) palladium (II)
Ph=Phenyl
$PhSO_2$=Phenyl sulfonyl
$PhSO_2Cl$=Phenyl sulfonyl chloride
PPA=Polyphosphoric acid
$PPh_3$ or $Ph_3P$=Tiphenyl phosphine
PTSA=p-Toluene sulfonic acid
t-Bu=t-Butyl
t-BuoCl=t-Butoxy chloride
t-BuOH=t-Butanol
t-BuOK=Potassium t-butoxide
t-BuONa=Sodium t-butoxide
TEA or $Et_3N$=Triethylamine
TFA=Trifluoroacetic acid
THF=Tetrahydrofuran As used herein, the term "disease or disorder modulated or mediated by an estrogen receptor" shall mean any disease or disorder which is mediated by the estrogen α, any disease or disorder which is mediated by the estrogen β receptor or any disease or disorder which is mediated by both the estrogen α and estrogen β receptors. For example, hot flashes, vaginal dryness, osteopenia, osteoporosis, hyperlipidemia, loss of cognitive function, a degenerative brain disorder, cardiovascular disease, cerebrovascular disease breast cancer, endometrial cancer, cervical cancer, prostate cancer, benign prostatic hyperplasia (BPH), endometriosis, uterine fibroids, osteoarthritis and contraception.

As used herein, the term "degenerative brain disease" shall include cognitive disorder, dementia (regardless of underlying cause) and Alzheimer's disease.

As used herein, the term "cardiovascular disease" shall include elevated blood lipid levels, coronary arteriosclerosis and coronary heart disease.

As used herein, the term "cerebrovascular disease" shall include abnormal regional cerebral blood flow and ischemic brain damage.

As used herein, the term "progestogen antagonist" shall include mifepristone (RU-486), J-867 (Jenapharm/TAP Pharmaceuticals), J-956 (Jenapharm/TAP Pharmaceuticals), ORG-31710 (Organon), ORG-32638 (Organon), ORG-31806 (Organon), onapristone (ZK98299) and PRA248 (Wyeth).

The term "subject" as used herein, refers to an animal, preferably a mammal, most preferably a human, who is the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention is directed to co-therapy comprising administration of one or more compound(s) of formula (I) or (II) and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula (I) and progestogen would be the amount of the compound of formula (I) and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula (I) or (II) with a progestogen or progestogen antagonist, wherein the compound(s) of formula (I) or (II) and the progestogen or progestogen antagonist are administered by any suitable means, simultaneously, sequentially, separately or in a single pharmaceutical formulation. Where the compound(s) of formula (I) or (II) and the progestogen or progestogen antagonist are administered in separate dosage forms, the number of dosages administered per day for each compound may be the same or different. The compound(s) of formula (I) or (II) and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) or (II) and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of formula (I) and (II) wherein $R^4$is oxo may be prepared according to the process outlined in Scheme 1.

Scheme 1

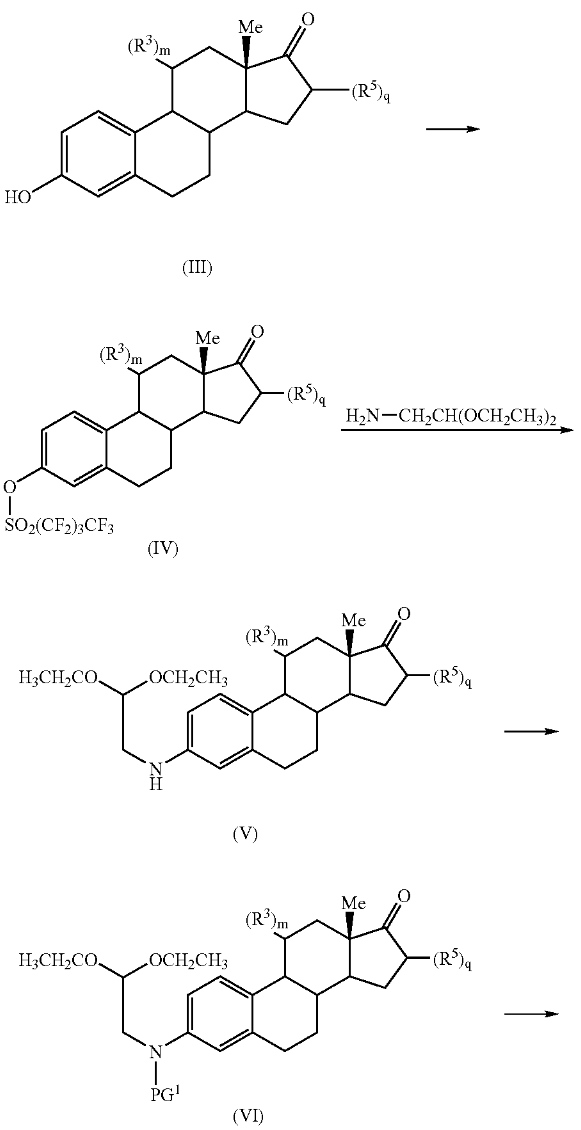

(III)

(IV)

(V)

(VI)

-continued

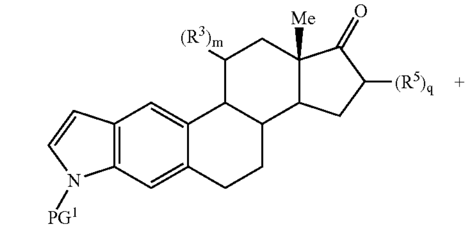

(VII)

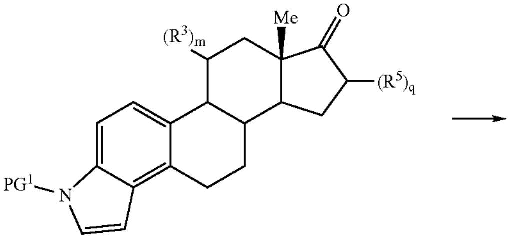

(VIII)

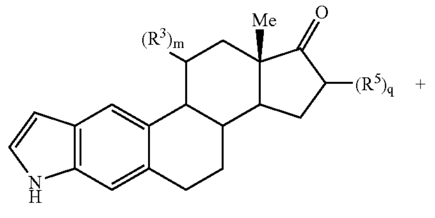

(Ia)

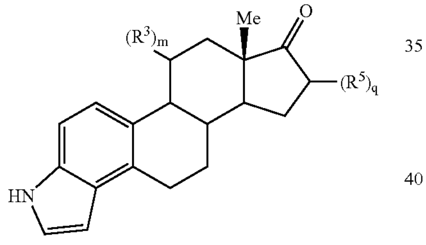

(IIa)

Accordingly, a suitably substituted compound of formula (III), a known compound or compound prepared by known methods, is reacted with 1,1,2,2,3,3,3-heptafluoro-propane-1-sulfonyl fluoride (i.e. $CF_3(CF_2)_3SO_2F$), a known compound, in the presence of a base such as TEA, DIPEA, pyridine, and the like, in an organic solvent such as DCM, THF, DMF, and the like, to yield the corresponding compound of formula (IV).

The compound of formula (IV) is reacted with 2,2-diethoxy-ethylamine, a known compound, in the presence of a phosphine ligand such as BINAP, DPPP, DPPE, and the like, in the presence of a catalyst such as $Pd(OAc)_2$, $Pd_2(dba)_3$, $Pd(PPh_3)_2Cl_2$, and the like, in the presence of a base such as sodium t-butoxide, $Cs_2CO_3$, $K_2CO_3$, and the like, to yield the corresponding compound of formula (V).

The compound of formula (V) is reacted with a suitable protecting agent, such as $CH_3SO_2Cl$, $PhSO_2Cl$, $CH_3COCl$, $(CF_3CO)_2O$, and the like, in the presence of a base such as TEA, DIPEA, pyridine, and the like, in an organic solvent such as DCM, THF, DMF, and the like, to yield the corresponding compound of formula (VI), wherein $PG^1$ is a protecting group such as $CH_3SO_2$, $PhSO_2$, Ac, $CF_3CO$, and the like, respectively.

The compound of formula (VI) is reacted with an acid such as PPA, PTSA, sulfuric acid, and the like, in an organic solvent such as toluene, xylene, and the like, to yield a mixture of the compound of formula (VII) and (VIII).

The compounds of formula (VII) and (VIII) are de-protected according to known methods, to yield the corresponding compounds of formula (Ia) and (IIa).

Preferably, the compounds of formula (Ia) and (IIa) are separated by known methods. Alternatively, the compounds of formula (VII) and (VIII) are separated by known methods, and then each is individually de-protected by known methods to yield the corresponding compounds of formula (Ia) and (IIa).

One skilled in the art will recognize that compounds of formula (I) and/or (II) wherein p is 2 and two $R^4$ groups are taken together as =N(OH) may be prepared from the corresponding compound of formula (I) and/or (II) respectively, wherein p is 2 and two $R^4$ groups are taken together as oxo by reacting the compound of formula (I) and/or (II) wherein p is 2 and two $R^4$ groups are taken together as oxo with hydroxylamine, in an organic solvent such as ethanol, methanol, isopropanol, and the like.

Compounds of formula (I) and/or (II) wherein $R^4$ is hydroxy may be prepared from the corresponding compound of formula (I) or (II) wherein $R^4$ is oxo. As an example, Scheme 2 describes a process for the preparation of compounds of formula (I) wherein $R^4$ is other than oxo.

Scheme 2

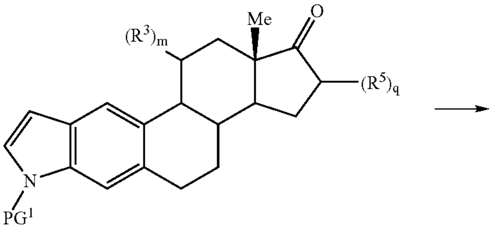

(VII)

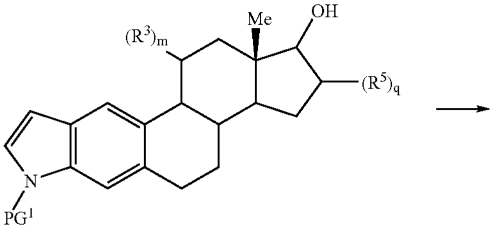

(IX)

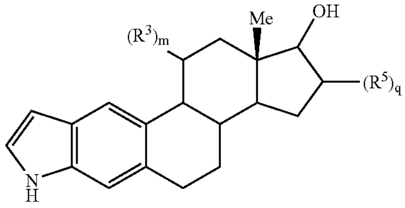

(Ic)

More specifically, a suitably substituted compound of formula (VII), prepared as in Scheme 1 above, is reduced with a reducing agent such as $NaBH_4$, $LiBH_4$, $LiAlH_4$, and the like, in a polar organic solvent such as methanol, ethanol, iso-propanol, and the like, to yield the corresponding compound of formula (IX).

The compound of formula (IX) is de-protected by known methods, to yield the corresponding compound of formula (Ic).

One skilled in the art will recognize that compounds of formula (II) wherein $R^4$ is hydroxy may be similarly prepared according to the process outlined in Scheme 2 by substituting the compound of formula (VIII) for the compound of formula (VII).

Compounds of formula (I) wherein p is 2 and $R^4$ is other than oxo or =N(OH) may be prepared according to the processes outlined in Scheme 3.

diethyl ether, dioxolane, and the like, to yield the corresponding compound of formula (XII). The use of a compound of formula (XI) is particularly preferred for introducing $R^4$ groups selected from -A, alkenyl, alkynyl, -alkenyl-A and -alkynyl-A.

The compound of formula (XII) is de-protected according to known methods, to yield the corresponding compound of formula (Id).

One skilled in the art will recognize that that compounds of formula (II) may be similarly prepared according to the process outlined in Scheme 3 by substituting the compound of formula (VIII) for the compound of formula (VII).

Compounds of formula (I) wherein p is 1 and $R^4$ is selected from —O-alkyl, —O-aralkyl, —O-cycloalkyl, —O-heterocycloalkyl or —O—C(O)-A may be prepared according to the process outlined in Scheme 4.

Scheme 3

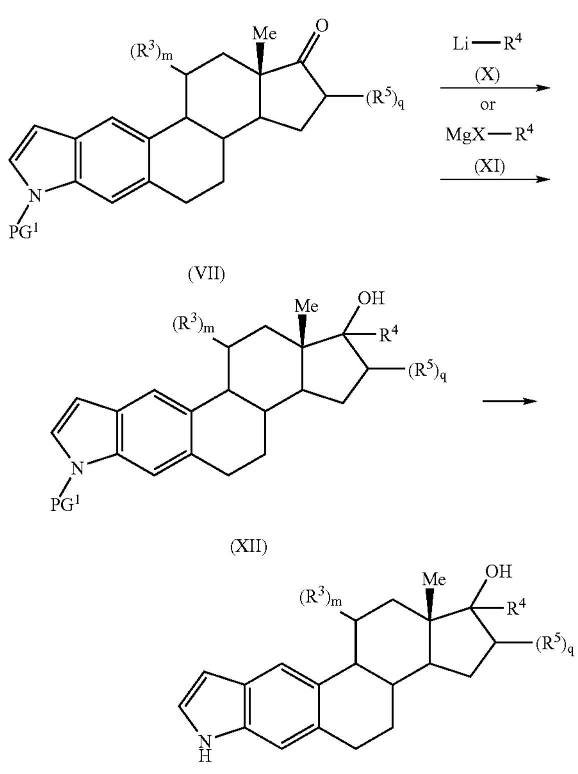

(VII)

(XII)

(Id)

Scheme 4

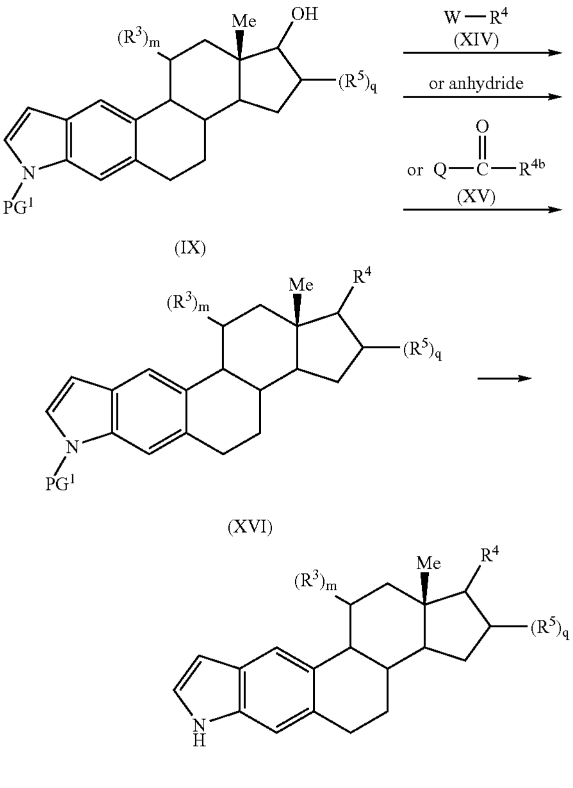

(IX)

(XVI)

(Ie)

Accordingly, a compound of formula (VII), prepared as in Scheme 1 above, is reacted with a suitably substituted compound of formula (X), in the presence of an organolithium agent such as alkyl lithium, aryl lithium, alkenyl lithium, alkynyl lithium, and the like, in an organic solvent such as THF, diethyl ether, and the like, to yield the corresponding compound of formula (XII). The use of a compound of formula (X) is particularly preferred for introducing $R^4$ groups selected from -A, alkenyl, alkynyl, -alkenyl-A and -alkynyl-A.

Alternatively, a compound of formula (VII), prepared as in Scheme 1 above, is reacted with suitably substituted compound of formula (XI), wherein X is Cl, Br or I, a Gringard agent such as alkyl magnesium halide, aryl magnesium halide, alkenyl magnesium halide, alkynyl magnesium halide, and the like, in an organic solvent such as THF, Accordingly, a compound of formula (IX), prepared as in Scheme 2 above, is reacted with suitably substituted compound of formula (XIV) wherein W is a leaving group such Cl, Br, I, tosylate, mesylate, triflate, and the like, and wherein $R^{4a}$ is selected from the group consisting of alkyl, aralkyl, cycloalkyl and heterocycloalkyl, in the presence of a base such as pyridine, TEA, imidazole, and the like, in an organic solvent such as DCM, THF, DMF, and the like, optionally in the presence of a catalyst agent such as DMAP, and the like, to yield the corresponding compound of formula (XVI) wherein $R^4$ is selected from —O-alkyl, —O-aralkyl, —O-cycloalkyl or —O-heterocycloalkyl.

Alternatively, a compound of formula (IX), prepared as in Scheme 2 above, is reacted with a suitably substituted anhydride (a compound of the formula $R^{4a}$—C(O)OC(O)—$R^{4a}$), wherein $R^{4a}$ is selected from the group consisting of alkyl, aralkyl, cycloalkyl, heterocycloalkyl and —C(O)-A in the presence of a base such as pyridine, TEA, imidazole, and the like, in an organic solvent such as DCM, THF, diethyl ether, and the like, optionally in the presence of a catalyst DMAP, and the like, to yield the corresponding compound of formula (XVI) wherein $R^4$ is selected from —O—C(O)-A.

Alternatively, a compound of formula (IX), prepared as in Scheme 2 above, is reacted with a suitably substituted compound of formula (XV), wherein Q is OH, Cl or Br, and wherein $R^{4b}$ is selected from the group consisting of alkyl, aralkyl, cycloalkyl and heterocycloalkyl, to yield the corresponding compound of formula (XVI). Wherein the compound of formula (XV) Q is Cl or Br, the compound of formula (IX) is reacted with the compound of formula (XV) in the presence of a base such as pyridine, TEA, imidazole, and the like, in an organic solvent such as DCM, THF, diethyl ether, and the like, optionally in the presence of a catalyst DMAP, and the like, to yield the corresponding compound of formula (XVI). Wherein the compound of formula (XV) Q is OH, the compound of formula (IX) is reacted with the compound of formula (XV) in the presence of a coupling agent such as DCC, DIC, and the like, in an organic solvent such as THF, diethyl ether, DCM, acetonitrile, and the like, to yield the corresponding compound of formula (XVI) wherein $R^4$ is selected from —O—C(O)-A.

The compound of formula (XVI) is de-protected according to known methods, to yield the corresponding compound of formula (Ie).

One skilled in the art will recognize that a compounds of formula (II) wherein p is 1 and $R^4$ is selected from —O-alkyl, —O-aralkyl, —O-cycloalkyl, —O-heterocycloalkyl or —O—C(O)-A may be similarly prepared according to the process outlined in Scheme 4 with substitution of a compound of formula (XIII)

(XIII)

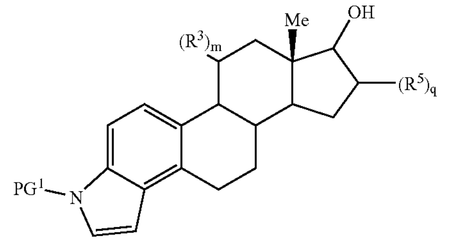

for the compound of formula (IX).

Compounds of formula (I) and (II) wherein n is 1 and the $R^2$ group is bound at the carbon atom adjacent to the N atom of the E ring may be prepared according to the process outlined in Scheme 5.

Scheme 5

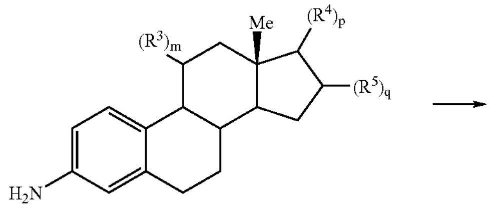

(XVII)

-continued

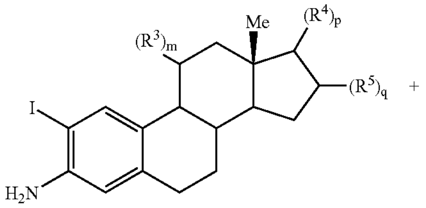

(XVIII)

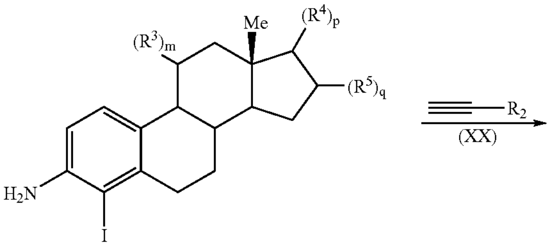

(XIX)

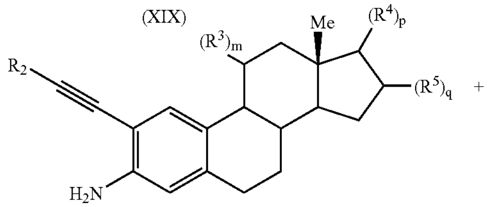

(XXI)

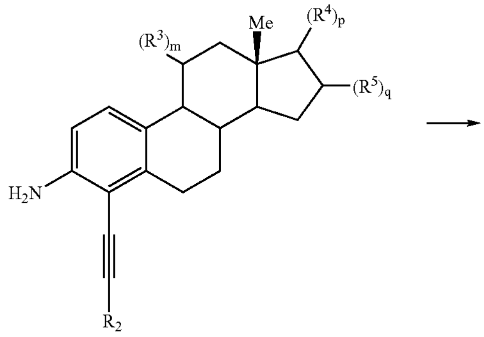

(XXII)

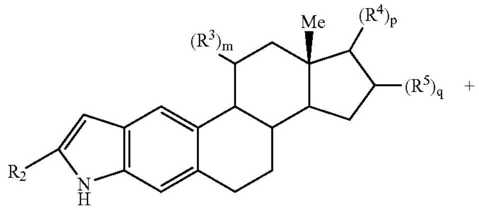

(If)

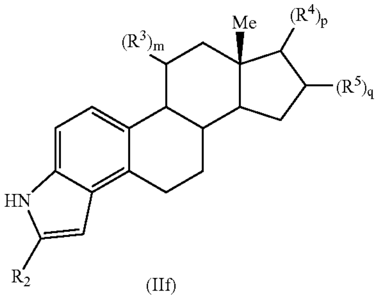

(IIf)

Accordingly, a suitably substituted compound of formula (XVII), a known compound or compound prepared by known methods, is reacted with an iodination agent such as NIS, iodine, ICI, and the like, in the presence of a coupling agent such as PTSA, and the like or a Lewis acid such as zinc chloride, $BF_3$·etherate, and the like, in an organic solvent such as methanol, ethanol, THF, DMSO, DMF, and the like, to yield a mixture of the corresponding compounds of formula (XVIII) and (XIX).

Optionally, the compounds of formula (XVIII) and (XIX) are separated by known methods.

The mixture of compounds of formula (XVIII) and (XIX) is reacted with a suitably substituted compound of formula (XX), a known compound or compound prepared by known methods, in the presence of a coupling agent such as $Pd(PPh_3)_2Cl_2$, $Pd(dba)_2$, and the like, optionally in the presence of CuI, in an organic solvent such as TEA, DIPEA, pyridine, and the like, optionally in an organic solvent such as methylene chloride, DCM, THF, benzene, and the like, to yield a mixture of the corresponding compounds of formula (XXI) and (XXII).

Optionally, the compounds of formula (XXI) and (XXII) are separated by known methods.

The mixture of the compounds of formula (XXI) and (XXII) is reacted with CuI in an organic solvent such as benzene, toluene, DMF, and the like, at an elevated temperature in the range of about 50 to about 110° C., to yield the corresponding compounds of formula (If) and (IIf).

Preferably, the compounds of formula (If) and (IIf) are separated by known methods.

Compounds of formula (I) and (II) wherein n is 1 and the $R^2$ group is bound at the carbon atom adjacent to the N atom of the E ring may alternatively be prepared according to the process outlined in Scheme 6.

Scheme 6

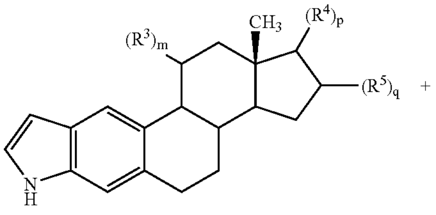

(Ib)

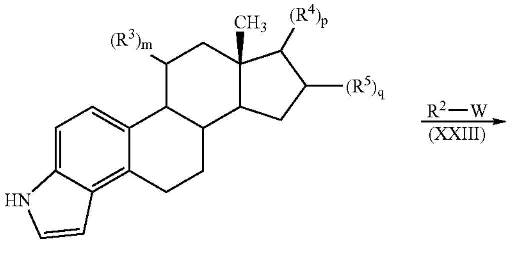

(IIb)

-continued

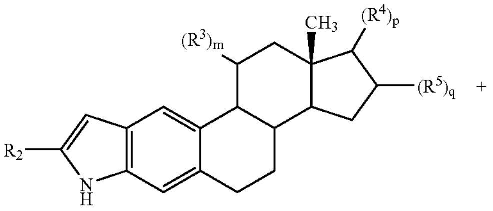

(Ic)

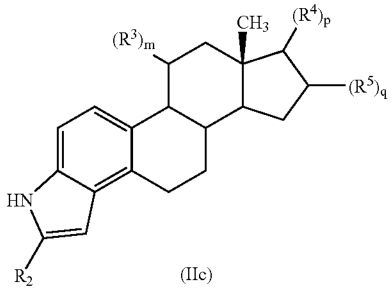

(IIc)

Accordingly, a suitably substituted compound of formula (Ib) or suitably substituted compound of formula (IIb) or mixture thereof (as exemplified herein), a known compound or compound prepared as described in the Schemes above, is reacted with a suitably substituted compound of formula (XXIII), wherein W is a leaving group such Cl, Br, I, tosylate, mesylate, triflate, and the like, a known compound or compound prepared by known methods, in the presence of a base such as LDA, LHMDS, t-butyl lithium, and the like, in an organic solvent such as THF, diethyl ether, dioxolane, and the like, to yield a mixture of the corresponding compounds of formula (Ic) and (IIc).

Preferably, the N atom on the E ring of the compound of formula (Ib) and (IIb) is protected by known methods prior to reacting with the compound of formula (XXIII) and then de-protected by known methods.

Preferably, the compounds of formula (Ic) and (IIc) are separated by known methods.

Compounds of formula (I) and (II) wherein n is 1 and the $R^2$ group is one carbon atom away form the N (i.e. at the beta position) or wherein n is 2 may be prepared according to the process outlined in Scheme 7.

Scheme 7

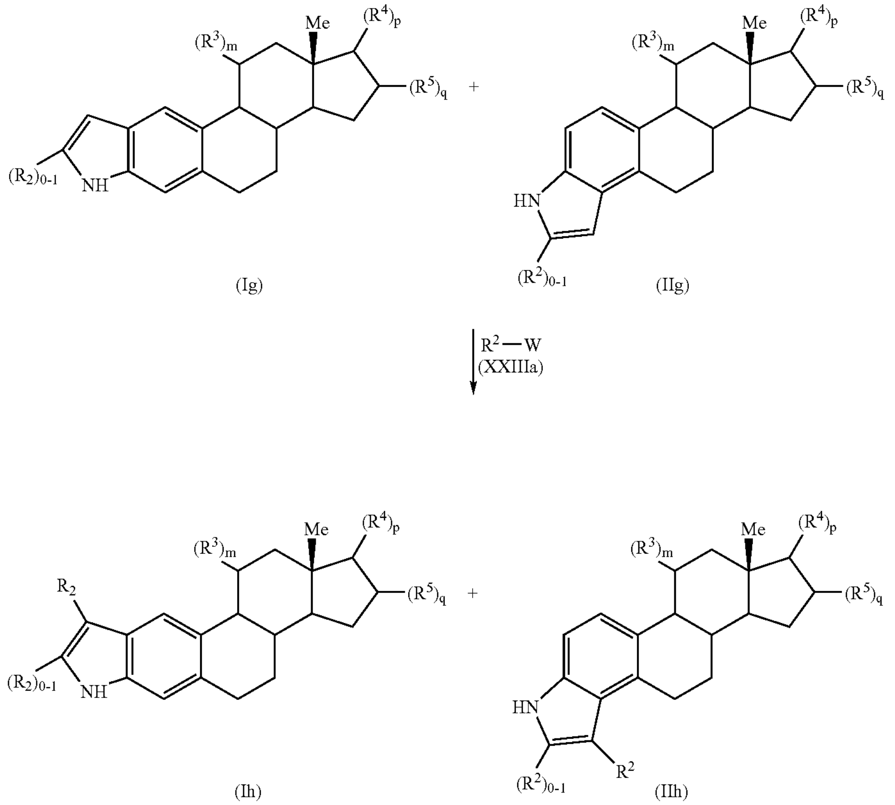

(Ig) (IIg) (Ih) (IIh)

Accordingly, a suitably substituted compound of formula (Ig) or compound of formula (IIg) or mixture thereof (as exemplified in the Scheme herein) is reacted with a suitably substituted compound formula (XXIII), wherein W is a leaving group such Cl, BR, I, tosylate, mesylate, triflate, and the like, a known compound or compound prepared by known methods, in the presence of a catalyst such as $AlCl_3$, $ZnCl_2$, and the like, in an organic solvent such as methylene chloride, DCM, benzene, and the like, to yield a mixture of the corresponding compounds of formula (Ih) and (IIh).

Preferably, the compounds of formula (Ih) and (IIh) are separated by known methods.

Compounds of formula (II) wherein n is 1, $R^2$ is selected from —S-A, and the $R^2$ group is bound to the carbon atom adjacent to the N atom (i.e. at the alpha position), may be prepared according to the process outlined in Scheme 8.

Scheme 8

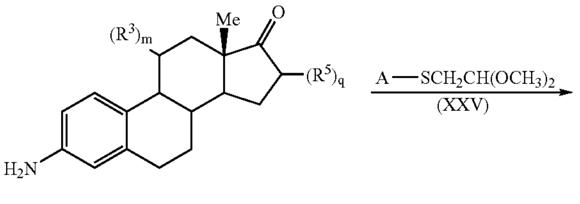

(XXIV)

-continued

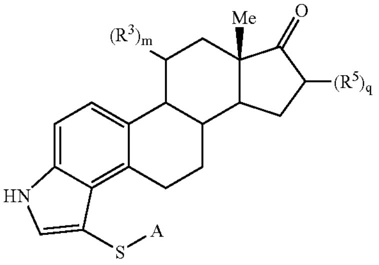

(IIj)

Accordingly, a compound of formula (XXIV), a known compound or compound prepared by known methods, is reacted with t-butoxy chloride and a compound of formula (XXV), a known compound or compound prepared by known methods, in the presence of a base such as TEA, DIPEA, pyridine, and the like, in an organic solvent such as DCM, chloroform, and the like, to yield the corresponding compound of formula (IIj).

Compounds of formula (I) wherein $R^1$ is selected from —OH or —O-A may be prepared according to the process outlined in Scheme 9.

Scheme 9

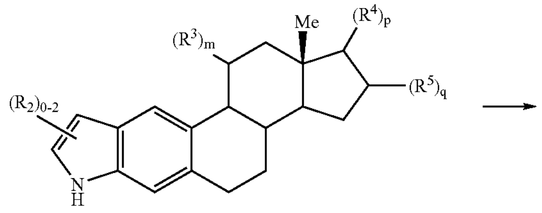

(Ik)

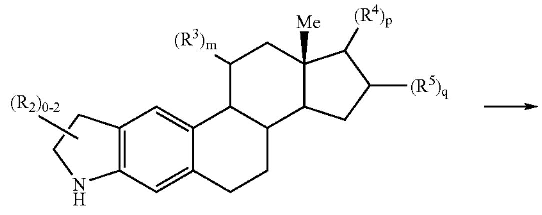

(XXVI)

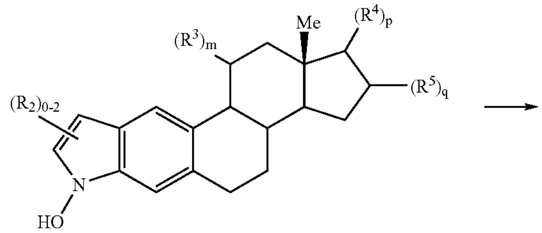

(Im)

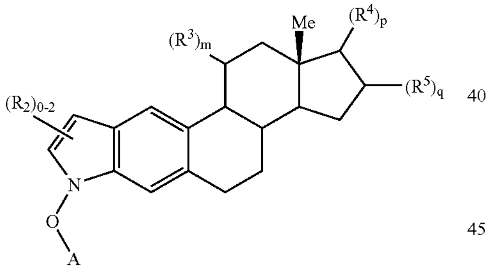

(In)

Accordingly, a suitably substituted compound of formula (Ik), is reacted with a reducing agent such as $H_2$, 1,4-cyclohexediene, triethylsilane, sodium cyanoboronhydride, borane, and the like, in the presence of an acid such as HCl, TFA, $BF_3$.etherate, and the like, in an organic solvent such as methanol, ethanol, THF and the like, to yield the corresponding compound of formula (XXVI).

The compound of formula (XXVI) is reacted with an oxidizing agent such as $H_2O_2$, NMO, and the like, in the presence of a catalysis such as $NaH_2PO_2$, $Na_2WO_4$, $NaIO_4$, and the like, in an organic solvent such as methanol, pyridine, AcOH, and the like, to yield the corresponding compound of formula (Im), a compound of formula (I) wherein the $R^1$ group is —OH.

The compound of formula (Im) is optionally reacted (to displace the H atom on the OH group) with a suitably substituted reagent such as A-halogen, A-tosylate, A-mesylate, A-triflate, A-C(O)-halogen, A-$SO_2$-halogen, a symmetric anhydride (e.g. A-C(O)OC(O)-A), an asymmetric anhydride (e.g. A-C(O)OC(O)-A'), a cyclic anhydride, and the like, in the presence of a base such as NaH, t-BuOK, NaOH and the like, in an organic solvent such as THF, DCM, dioxlane, DMSO, DMF and the like, to the corresponding compound of formula (In), a compound of formula (I) wherein the $R^1$ group is O-A, —C(O)-A or —$SO_2$-A.

Compounds of formula (I) wherein $R^1$ is selected from -A, —C(O)-A or —$SO_2$-A may be prepared according to the process outlined in Scheme 10.

Scheme 10

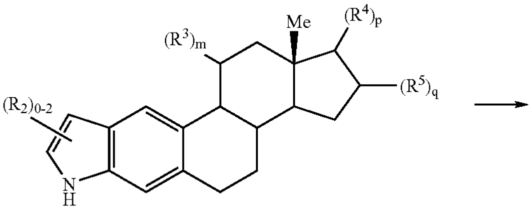

(Ik)

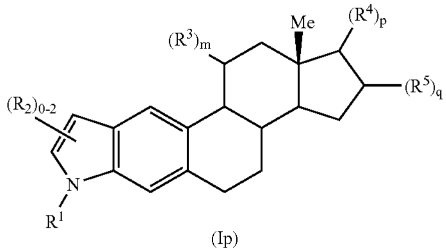

(Ip)

Accordingly, a suitably substituted compound of formula (Ik), is reacted with a suitably substituted reagent such as A-C(O)-halogen, A-$SO_2$-halogen, an asymmetric anhydride (e.g. A-C(O)OC(O)-A'), a symmetric anhydride (e.g. A-C(O)OC(O)-A), a cyclic anhydride, and the like, in the presence of a base such as NaH, t-BuOK, NaOH and the like, in an organic solvent such as THF, DCM, dioxlane, DMSO, DMF and the like, to yield the corresponding compound of formula (Ip), wherein the $R^1$ group is selected from -A (wherein A is other than aryl or heteroaryl), —C(O)-A or —$SO_2$-A.

For compounds of formula (I) wherein $R^1$ is -A and A is vinyl, aryl or heteroaryl, the compounds of formula (Ik) is reacted with a suitably substituted reagent such as vinyl-halide, (aryl or heteroaryl)-halide, (aryl or heteroaryl)-triflate, in the presence of a catalyst such as $Pd(OAc)_2$, $Pd(PPh_3)_2Cl_2$, $Pd_2(dba)_3$, CuI, CuBr and the like, in the presence of a base such as $Cs_2CO_3$, t-BuONa, CsF, $K_2CO_3$ and the like, in the presence of a ligand such as DPPP, DPPE, $Ph_3P$, BINAP and the like, in an organic solvent such as toluene, dioxlane, DMF and the like, to yield the corresponding compound of formula (Ip), wherein the $R^1$ is A and A is vinyl, aryl or heteroaryl.

One skilled in the art will recognize that compounds of formula (II) wherein $R^1$ is selected from —OH, —O-A, -A, —C(O)-A or —$SO_2$-A may be similarly prepared according to the processes outlined in Scheme 9 and 10 with substitution of a suitably substituted compound of formula (IIk)

(IIk)

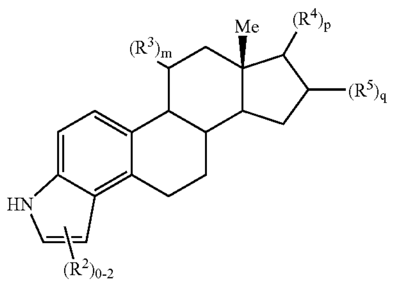

for the compound of formula (Ik). One skilled in the art will further recognize that a mixture of a compound of formula (Ik) and a compound of formula (IIk) may be substituted for the compound of formula (Ik) in Schemes 9 and 10 above, to yield a mixture of the corresponding compounds of formula (I) and (II) wherein $R^1$ is selected from —OH, —O-A, -A, —C(O)-A or $SO_2$-A. Wherein a mixture is reacted in Scheme 9 or 10, the resultant mixture of compounds of formula (I) and (II) is preferably separated, according to known methods.

Compounds of formula (I) wherein n is 1 and $R^2$ is selected from the group consisting of halogen, cyano, aryl, heteroaryl, —$SO_2$—$NH_2$, —$SO_2$—NH(alkyl) and —$SO_2$—N(alkyl)$_2$, and wherein the $R^2$ group is bound at the carbon atom adjacent to the N atom of the E ring, may be prepared according to the process outlined in Scheme 11.

Scheme 11

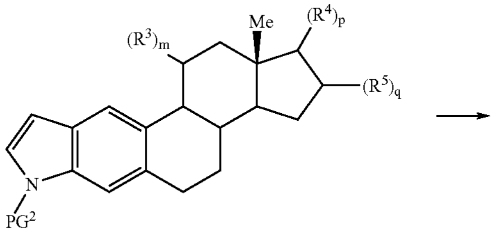

(XXX)

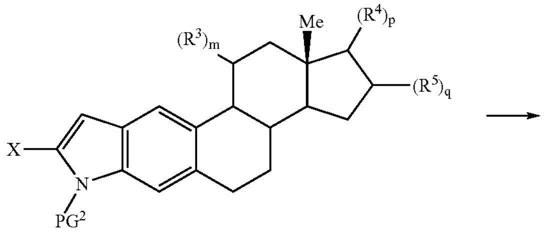

(XXXI)

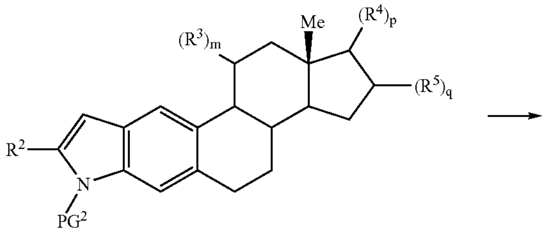

(XXXVI)

-continued

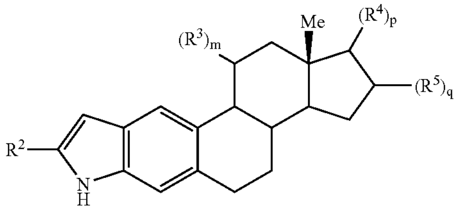

(Iq)

Accordingly, a suitably substituted compound of formula (XXX), wherein $PG^2$ is a suitably protecting group, is reacted with a halide source such as iodine, bromide, NIS, NBS, and the like, in the presence of a base such as LDA, LiHMDS, t-BuOk, and the like, in an organic solvent such as THF, diethyl ether, dioxlane, and the like, to yield the corresponding compound of formula (XXXI), wherein X is the corresponding halogen (for example when the halide source is iodine or NIS, then X is —I; when the halide source is bromine, NBS, then X is —Br).

The compound of formula (XXXI) is reacted with a coupling agent such as CuCN, and the like, optionally in the presence of a base such as diethylpropyl amine, N-methylpyrrolidone, and the like, in an organic solvent such as THF, DMF, DMSO, and the like, to yield the corresponding compound of formula (XXXVI), which is then de-protected by known methods; to yield the corresponding compound of formula (Iq), wherein the $R^2$ group is CN group.

Alternatively, the compound of formula (XXXI) is reacted with CO, in the presence of a catalyst such as $Pd(OAc)_2$, $Pd(PPh_3)_2Cl_2$, $Pd_2(dba)_3$, and the like, in the presence of a base such as $Et_3N$, $Bu_3N$, $K_2CO_3$ and the like, in the presence of a ligand such as DPPP, DPPE, $Ph_3P$, BINAP and the like, and then treated with a trapping agent such as $H_2O$, or an alcohol of the formula A-OH, such as MeOH, t-BuOH, phenol, and the like, in an organic solvent such as toluene, dioxlane, DMF and the like, to yield the corresponding compound of formula (XXXVI), which is then de-protected by known methods; to yield the corresponding compound of formula (Iq), wherein the $R^2$ group is carboxy (when the trapping agent is $H_2O$) or —C(O)—O-A (when the trapping agent is an alcohol).

Alternatively, the compound of formula (XXXI) is reacted with a suitably substituted organometallic agent such as an aryl or heteroaryl Grignard (a compound of the formula (aryl or heteroaryl)-Mg-halogen), a suitably substituted stannyl group (a compound of the formula (aryl or heteroaryl)Sn(alkyl)$_3$), a suitably substituted boronic acid (a compound of the formula (aryl or heteroaryl)-B(OH)$_2$) or a suitably substituted boronic ester (a compound of the formula (aryl or heteroaryl)-B(O-alkyl)$_2$), and the like, in the presence of a catalyst such as $Pd(OAc)_2$, $Pd(PPh_3)_2Cl_2$, $Pd_2(dba)_3$, and the like, a base such as $Et_3N$, $Bu_3N$, $K_2CO_3$ and the like, a ligand such as DPPP, DPPE, $Ph_3P$, BINAP and the like, in an organic solvent such as toluene, dioxlane, DMF and the like, to yield the corresponding compound of formula (XXXVI), which is then de-protected by known methods; to yield the corresponding compound of formula (Iq) wherein the $R^2$ group is aryl or heteroaryl.

Alternatively, the compound of formula (XXXI) is reacted with a suitably substituted nitrogen containing compound, in the presence of a catalyst such as $Pd(OAc)_2$, $Pd(PPh_3)_2Cl_2$, $Pd_2(dba)_3$, and the like, a base such as t-BuONa, $K_3PO_4$, $Cs_2CO_3$, $K_2CO_3$ and the like, a ligand such as DPPP, DPPE, $Ph_3P$, BINAP and the like, in an organic solvent such as toluene, dioxlane, DMF and the like, to yield the corresponding compound of formula (XXXVI), which is then de-protected by known methods; to yield the corresponding compound of formula (Iq) wherein the $R^2$ group is selected from amino, alkylamino, dialkylamino, aminocarbonyl, alkylaminocarbonyl or dialkylaminocarbonyl.

One skilled in the art will recognize that compounds of formula (I) wherein $R^2$ is —$SO_2$—$NH_2$, —$SO_2$—NH(alkyl) or —$SO_2$—N(alkyl)$_2$ may be similarly prepared by reacting a suitably substituted compound of formula (XXX) with chlorosulfonic acid, in an organic solvent such as THF, diethyl ether, DCM, DMF, and the like, and then displacing the chlorine atom by quenching with a suitably substituted amine.

Compounds of formula (I) wherein n is 1 and $R^2$ is selected from the group consisting of halogen, cyano, aryl, heteroaryl, —$SO_2$—$NH_2$, —$SO_2$—NH(alkyl) and —$SO_2$—N(alkyl)$_2$, and wherein the $R^2$ group is bound at the carbon atom one carbon atom removed from the N atom of the E ring, may be prepared similarly prepared according to the process outlined in Scheme 11. More particularly, the compound of formula (XXX) is reacted with a halide source such as iodine, bromide, NIS, NBS, and the like, in an organic solvent such as THF, diethyl ether, dioxlane, and the like, to yield the corresponding compound of formula (XXXII), (XXXII)

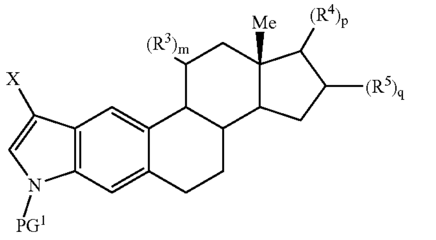

wherein X is the corresponding halogen (for example when the halide source is iodine or NIS, then X is —I; when the halide source is bromine, NBS, then X is —Br). The compound of formula (XXXII) is then reacted according to the process outlined above to displace the halogen atom with the desired $R^2$ group.

Compounds of formula (I) wherein n is 1 and $R^2$ is selected from the group consisting of —OH, —O-A, —S-A, —SO-A or $SO_2$-A may be prepared according to the process outlined in Scheme 12.

Scheme 12

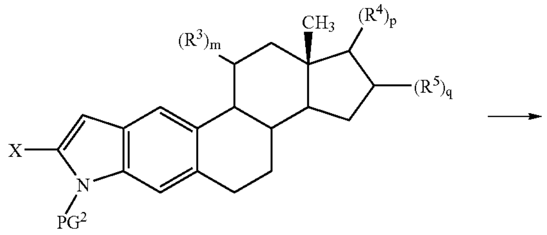

(XXXI)

-continued

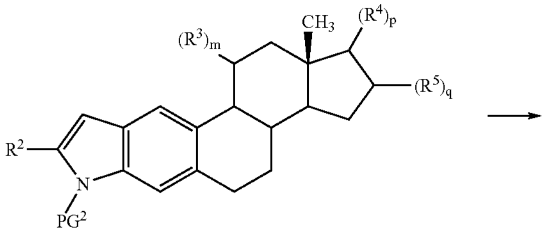

(XXXIII)

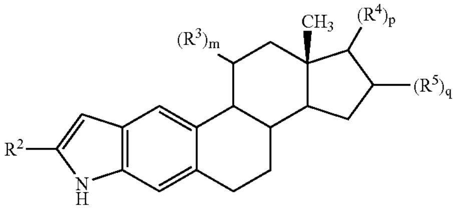

(Ir)

Accordingly, a suitably substituted compound of formula (XXXI), wherein $PG^2$ is a suitably protecting group, and wherein X is Cl, Br or I, is reacted with a coupling agent such as CuI, NiBr, and the like, in the presence of a suitably substituted alcohol, a compound of the formula A-OH, or a suitably substituted compound of the formula A-SH, in an organic solvent such as THF, DMF, toluene, dioxlane, and the like, optionally in the presence of a catalyst such as $Pd(OAc)_2$, $Pd(PPh_3)_2Cl_2$, $Pd_2(dba)_3$, and the like, to yield the corresponding compound of formula (XXX(III), wherein $R^2$ is —O-A or —S-A, respectively.

When in the compound of formula (XXX(III), $R^2$ is —S-A, the compound of formula (XXXIII) may be optionally reacted with an oxidizing agent such as oxone, mCPBA, $H_2O_2$, and the like, in a solvent such as MeOH, THF, $H_2O$, and the like, to yield the corresponding compound wherein the $R^2$ group is selected from —SO-A or —$SO_2$-A.

The compound of formula (XXXIII) is de-protected by known methods, to yield the corresponding compound of formula (Ir).

One skilled in the art will recognize that the processes outlined in Schemes 11 and 12 may be similarly applied to the preparation of compounds of formula (II) by substitution of a suitably substituted compound of formula (XXXIV)

(XXXIV)

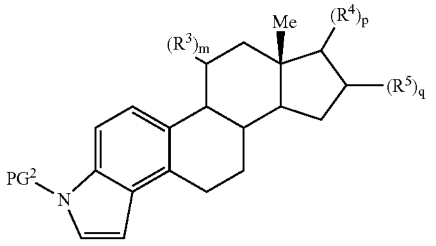

for the compound of formula (XXX) in Scheme 11 and substitution of a suitably substituted compound of formula (XXXV)

(XXXV)

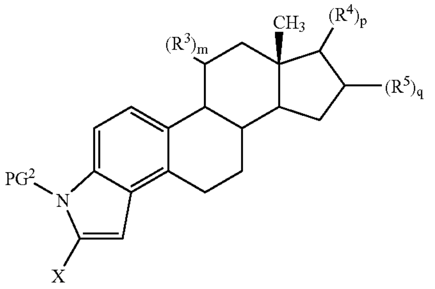

for the compound of formula (XXXI) in Scheme 12. One skilled in the art will further recognize that the processes in Schemes 11 and 12 may similarly be applied to yield a mixture of compounds of formula (I) and (II) by substitution of a mixture of suitably substituted compounds of formula (XXX) and (XXXIV) in Scheme 11 and a mixture of suitably substituted compounds of formula (XXXI) and (XXXV) in Scheme 12. Wherein the processes are applied to yield a mixture of compounds of formula (I) and (II), preferably, the compounds of formula (I) and (II) are separated by known methods.

One skilled in the art will further recognize that the processes described in the Schemes outlined herein may be carried out in any combination which will yield a compound of formula (I) or (II) with the desired substituent groups.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The utility of the compounds of the instant invention to treat disorders mediated by an estrogen receptor may be determined according to the procedures described in Examples 18, 19, 20 and 21 herein.

The present invention therefore provides a method of treating disorders mediated by an estrogen receptor in a subject in need thereof which comprises administering any of the compounds as defined herein in a quantity effective to treat said disorder. The compound may be administered to a patient by any conventional route of administration, including, but not limited to, intravenous, oral, subcutaneous, intramuscular, intradermal and parenteral. The quantity of the compound which is effective for treating a disorder mediated by an estrogen receptor is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by an estrogen receptor described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of this invention may be administered in any of the foregoing compositions and according to dosage regimens established in the art whenever treatment of a disorder mediated by an estrogen receptor is required.

The daily dosage of the products may be varied over a wide range from 5 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

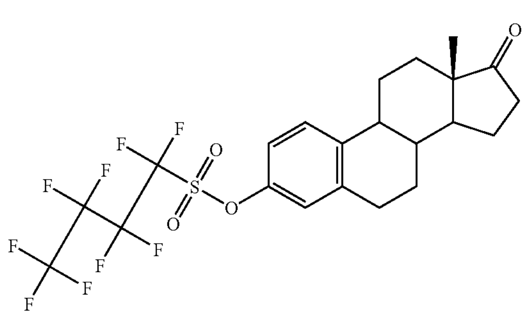

$CF_3(CF_2)_3SO_2F$ (27.7 mmol, 4.97 mL) was added dropwise through a syringe into a solution of estrone (18.5 mmol, 5.0 g) and TEA (27.7 mmol, 3.90 mL) in $CH_2Cl_2$ (100 mL)

at 0° C. The reaction mixture was slowly warmed to room temperature over 2 h. The solution was then washed with saturated $NaHCO_3$ and brine, then dried over anhydrous $Na_2SO_4$, filtered and concentrated to yield a white solid. The white solid was purified by flash chromatography using 4:1 hexanes/EtOAc to yield the title compound as a white solid.

$^1H$ NMR (300 MHz, $CDCl_3$) δ 7.35 (d, J=9.0 Hz, 1H), 7.05 (d, J=9.0 Hz, 1H), 7.01 (s, 1H), 2.95 (m, J=4.1 Hz, 2H), 2.42 (dd, J=18.0, 8.8 Hz, 1H), 2.38 (m, 1H), 2.30 (m, 1H), 2.15 (dd, J=17.6, 8.8 Hz, 1H), 2.10~1.99 (m, 3H), 1.77~1.51 (m, 6H), 0.98 (s, 3H) MS (m/z) $MH^-$ (551).

EXAMPLE 2

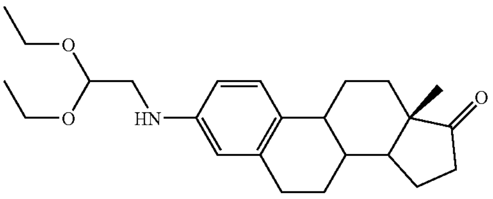

A three-neck flask was charged with $Pd(OAc)_2$ (0.0182 mmol, 4.1 mg), BINAP (0.02 mmol, 12 mg) and NaO-t-Bu (1.274 mmol, 122 mg). The reaction mixture was stirred in toluene (20 mL) for 10 min at 80° C. A mixture of $NH_2CH_2CH(OCH_2CH_3)_2$ (1.092 mmol, 159 μL) and the compound prepared as in Example 1 (0.91 mmol, 500 mg) in toluene (2 mL) was then slowly added dropwise via syringe to the reaction mixture. After addition, the mixture was heated at 80° C. with stirring for 2 h. The reaction mixture was cooled to room temperature. $Et_2O$ and water were added and the solution was partitioned between $Et_2O$ and water. The $Et_2O$ layer was washed with brine, dried over anhydrous $Na_2SO_4$ and concentrate to yield the title compound as a crude solid. The crude product was purified by column chromatography using 4:1 hexanes/EtOAc to yield the title compound as a colorless oil.

$^1H$ NMR (300 MHz, $CDCl_3$) δ 7.12 (d, J=8.8 Hz, 1H), 6.53 (d, J=8.8 Hz, 1H) 6.38 (s, 1H), 4.68 (t, J=6.0 Hz, 1H), 3.80 (br, s, 1H), 3.75 (m, 2H), 3.60 (m, 2H), 3.22 (d, J=6.0 Hz, 2H), 2.91 (m, 2H), 2.50 (dd, J=18.0, 8.8 Hz, 1H), 2.42 (m, 1H), 2.35 (m, 1H), 2.20 (m, 1H), 2.15~1.94 (m, 3H), 1.72~1.38 (m, 6H), 1.25 (t, J=7.6 Hz, 6H), 0.98 (s, 3H) MS (m/z) M+Na (408), $MH^-$ (384).

EXAMPLE 3

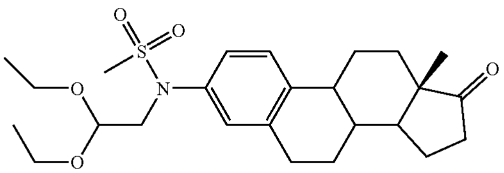

Pyridine (5.52 mmol, 446 μL) was added dropwise via syringe into a solution of the compound prepared as in Example 2 (3.68 mmol, 1.417 g) in $CH_2Cl_2$ (50 mL) at 0° C., followed by addition of $CH_3SO_2Cl$ (4.42 mmol, 342 μL). The reaction mixture was then stirred and warmed to room temperature over 2 h. The solution was partitioned between $CH_2Cl_2$ and saturated $NaHCO_3$. The organic layer was washed with brine and dried over anhydrous $Na_2SO_4$, filtered and concentrated to yield the title compound as a colorless oil. The product was sufficiently pure to be used in the next step without further purification.

$^1H$ NMR (300 MHz, $CDCl_3$) δ 7.28 (d, J=9.0 Hz, 1H), 7.15 (d, J=9.0 Hz, 1H), 7.10 (s, 1H), 4.61 (t, J=5.5 Hz, 1H), 3.75 (d, J=5.5 Hz, 2H), 3.62 (m, 2H), 3.54 (m, 2H), 3.05 (s, 3H), 2.91 (m, 1H), 2.55 (m, 1H), 2.40 (m, 1H), 2.22 (dd, J=17.5, 8.0 Hz, 1H), 2.15~1.95 (m, 4H), 1.75~1.38 (m, 6H), 1.15 (t, J=7.5 Hz, 6H), 0.94 (s, 3H) MS (m/z) $MH^+$ (464).

EXAMPLE 4

Compounds #1 and #2

(E4a)

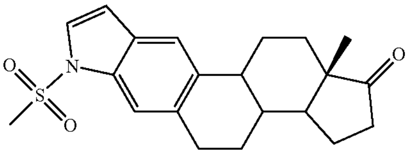

and (E4b)

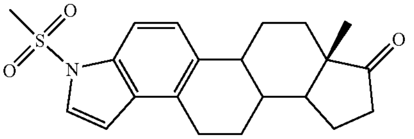

A mixture of the compound prepared in Example 2 (887 mg, 1.916 mmol) in toluene (15 mL) was treated with PPA (~1.0 g). The reaction mixture as then heated to reflux for 2 h. The reaction mixture was then cooled to room temperature, the solution was washed with water, saturated $NaHCO_3$ and rine and then dried over anhydrous $Na_2SO_4$. The resulting salt was filtered off and the solution was concentrated to afford a mixture of the title compounds as a clean oil. The oil was purified by chromatography (Biotage) using $CH_2Cl_2$ as eluent to yield the title compounds.

(E4a):

$^1H$ NMR (300 MHz, $CDCl_3$) δ 7.68 (s, 1H), 7.55 (s, 1H), 7.36 (d, J=3.2 Hz, 1H), 6.67 (d, J=3.2 Hz, 1H), 3.20~3.00 (m, 2H), 3.10 (s, 3H), 2.62~2.50 (m, 2H), 2.45 (m, 1H), 2.32~2.01 (m, 4H), 1.75~1.45 (m, 6H), 0.98 (s, 3H); MS (m/z) $MH^+$ (373).

(E4b):

$^1H$ NMR (300 MHz, $CDCl_3$) δ 7.75 d, J=7.5 Hz, 1H), 7.42 9d, J=3.0 Hz, 1H), 7.39 (d, J=7.5 Hz, 1H), 6.70 (d, J=3.0 Hz, 1H), 3.21~3.02 (m, 2H), 3.11 (s, 3H), 2.60~2.38 (m, 3H), 2.28~1.98 (m, 4H), 1.83~1.48 (m, 6H), 0.98 (s, 3H) MS (m/z) $MH^+$ (373).

EXAMPLE 5

Compound #3

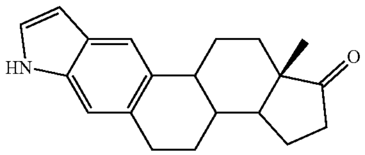

A mixture of Compound #1, prepared as in Example 3, (48 mg, 0.13 mmol) in 5% KOH in EtOH solution (1 mL) was heated at reflux for 6 h. The reaction mixture was then cooled to room temperature, the solvent removed in. vacuo and the residue partitioned between EtOAc and water. The aqueous layer was extracted with EtOAc three times. The combined organic layer was then washed with saturated $NH_4Cl$, water and brine, then dried over anhydrous $Na_2SO_4$, filtered and concentrated to yield the title compound as a crude solid. The solid was purified by flash chromatography using $CH_2Cl_2$ to yield the title compound as white solid.

$^1$H NMR (300 MHz, $CDCl_3$) δ 8.02 (br, s1H), 7.58 (s, 1H), 7.18 (s, 1H), 7.16 (d, J=3.0 Hz, 1H), 6.45 (d, J=4.5 Hz, 1H), 3.05 (m, J=6.0 Hz, 2H), 2.58~2.35 (m, 3H), 2.25~1.97 (m, 4H), 1.78~1.45 (m, 6H), 0.92 (s, 3H) MS (m/z) M+Na (316), $MH^+$ (294).

EXAMPLE 6

Compound #4

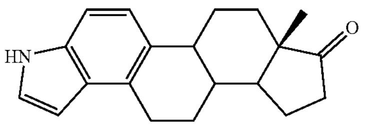

Compound #2, prepared as in Example 3 (54 mg, 0.145 mmol) in 5% KOH in EtOH solution (1 mL) was heated at reflux for 6 h. The reaction mixture was then cooled to room temperature, the solvent was removed in vacuo and the residue was partitioned between EtOAc and water. The aqueous layer was extracted with EtOAc three times. The combined organic layer was then washed with sat. $NH_4Cl$, water and brine, then dried over anhydrous $Na_2SO_4$, filtered and concentrated to yield the title compound as a crude solid. The solid was purified by flash chromatography using $CH_2Cl_2$ to yield the title compound as a white solid.

$^1$H NMR (300 MHz, $CDCl_3$) δ 8.15 (br, s, 1H), 7.24 (s, 1H), 7.22 (s, 1H), 7.20 (d, J=3.0 Hz, 1H), 6.52 (d, J=3.0 Hz, 1H), 3.25~3.01 (m, 2H), 2.65~2.38 (m, 3H), 2.25~1.90 (m, 4H), 1.82~1.48 (m, 6H), 0.92 (s, 3H) MS (m/z) $MH^+$ (294).

EXAMPLE 7

Compound #7

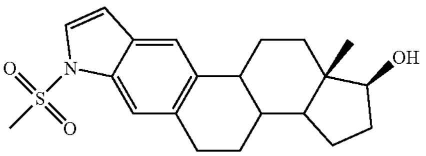

$NaBH_4$ (1.56 mmol, 59 mg) was added in one portion into a mixture of Compound #1, prepared as in Example 3 (58 mg, 0.156 mmol) in MeOH (2 mL) at 0° C. The reaction mixture was warmed to room temperature over 10 min. The solvent was removed in vacuo and the residue was partitioned between $CH_2Cl_2$ and water. The aqueous layer was extracted with $CH_2Cl_2$ twice. The combined organic layer was then washed with brine, dried over anhydrous $Na_2SO_4$, filtered and concentrated to yield the title compound as a crude solid. The solid was purified by flash chromatography using 3:1 hexanes/EtOAc to yield the title compound as a white solid.

$^1$H NMR (300 MHz, $CDCl_3$) δ 7.65 (s, 1H), 7.59 (s, 1H), 7.32 (d, J=4.0 Hz, 1H), 6.65 (d, J=4.0 Hz 1H), 3.78 (t, J=9.0 Hz, 1H), 3.10 (s, 3H), 3.12~3.01 (m, 2H), 2.82~2.78 (m, 1H), 2.41~2.22 (m, 2H), 2.20~2.11 (m, 1H), 1.98~1.92 (m, 1H), 1.85~1.60 (m, 2H), 1.59~1.25 (m, 6H), 0.85 (s, 3H) MS (m/z) $MH^+$ (375).

EXAMPLE 8

Compound #5

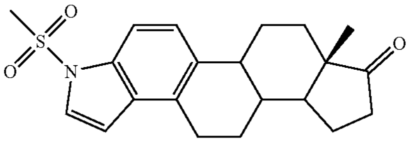

$NaBH_4$ (2.13 mmol, 81 mg) was added one portion into a mixture of Compound #2, prepared as in Example 3 (79 mg, 0.213 mmol) in MeOH (3 mL) at 0° C. The reaction mixture was warmed to room temperature over 10 min. The solvent was removed in vacuo and the residue was partitioned between $CH_2Cl_2$ and water. The aqueous layer was extracted with $CH_2Cl_2$ twice. The combined organic layer was then washed with brine, dried over anhydrous $Na_2SO_4$, filtered and concentrated to yield the title compound as a crude solid. The solid was purified by flash chromatography purification 3:1 hexanes/EtOAc to yield the title compound as a white solid.

$^1$H NMR (300 MHz, $CDCl_3$) δ 7.66 (d, J=9.5 Hz, 1H), 7.35 (d, J=3.5 Hz, 1H), 7.28 (d, J=9.5 Hz, 1H), 6.65 (d, J=3.5 Hz, 1H), 3.70 (t, J=9.0 Hz, 1H), 3.05 (s, 3H), 3.10~2.85 (m, 2H), 2.55~2.25 (m, 3H), 2.15~2.02 (m, 2H), 2.00~1.85 (m, 2H), 1.80~1.42 (m, 6H), 0.90 (s, 3H) MS (m/z) $MH^+$ (375).

EXAMPLE 9

Compound #8

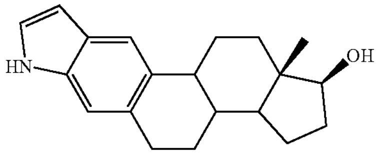

A mixture of Compound #7, prepared as in Example 7(51 mg, 0.137 mmol) in 5% KOH in EtOH solution (2 mL) was refluxed for 2 h. The reaction mixture was then cooled to room temperature, the solvent was removed in vacuo and the residue was partitioned between $CH_2Cl_2$ and water. The aqueous layer was extracted with $CH_2Cl_2$ twice. The combined organic layer was then washed with saturated $NH_4Cl$, water and brine, then dried over anhydrous $Na_2SO_4$, filtered and concentrated to yield the title compound as a crude solid. The solid was purified by flash chromatography using 2:1 hexanes/EtOAc to yield the title compound as a white solid.

$^1$H NMR (300 MHz, $CDCl_3$) δ 8.01 (br, s, 1H), 7.68 (s, 1H), 7.14 (s, 1H), 7.12 (d, J=3.5 Hz, 1H), 6.45 (d, J=3.5 Hz, 1H), 3.75 (t, J=8.5 Hz, 1H), 3.05~2.95 (m, 2H), 2.52 (m, 1H), 2.43 (m, 1H), 2.15 (m, 1H), 2.05~1.88 (m, 2H), 1.80~1.58 (m, 2H), 1.55~1.28 (m, 6H), 0.85 (s, 3H) MS (m/z) M+Na (318), $MH^+$ (296).

EXAMPLE 10

Compound #6

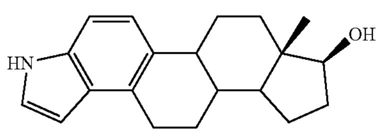

Compound #5, prepared as in Example 8 (71 mg, 0.190 mmol) in 5% KOH in EtOH solution (2 mL) was refluxed for 2 h. After the reaction was cooled down to room temperature, the solution was removed in vacuo and the residue was partitioned between $CH_2Cl_2$ and water. The aqueous layer was extracted with $CH_2Cl_2$ twice. The combined organic layer was then washed with saturated $NH_4Cl$, water and brine, then dried over anhydrous $Na_2SO_4$, filtered and concentrated to generate a clean solid. The solid was purified by flash chromatography using 2:1 hexanes/EtOAc to yield the title compound as white solid.

$^1$H NMR (300 MHz, $CDCl_3$) δ 8.05 (br, s, 1H), 7.15 (s, 1H), 7.13 (s, 1H), 7.12 (d, J=3.5 Hz, 1H), 6.45 (d, J=3.5 Hz, 1H), 4.65 (t, J=9.5 Hz, 1H), 3.10~2.90 (m, 2H), 2.40~2.28 (m, 2H), 2.20~2.08 (m, 1H), 1.98 (m, 1H), 1.85 (m, 1H), 1.78 (m, 1H), 1.65 (m, 1h), 1.60~1.28 (m, 6H), 0.85 (s, 3H) MS (m/z) M+Na (318), $MH^-$ (294).

EXAMPLE 11

Compound #10

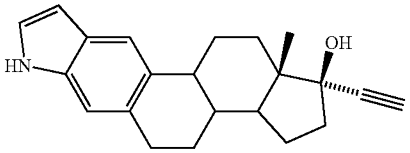

Lithium acetylide-ethylenedimine complex (46 mg, 0.523 mmol) was added into a mixture of Compound #1, prepared as in Example 4 (45 mg, 0.153 mmol) in dry dioxane (1 mL) and DMSO (1 mL) at room temperature. The reaction mixture was stirred for 1 h. The solvent was removed and then EtOAc and water were added. The mixture was partitioned between EtOAc and water. The organic layer was washed with water and brine, then dried over anhydrous $Na_2SO_4$, filtered and concentrated to yield the title compound as a crude yellow oil. The oil was purified by flash chromatography using 2:1 hexanes/EtOAc to yield the title compound as a yellowish oil.

$^1$H NMR (300 MHz, $CDCl_3$) δ 8.00 (br, s, 1H), 7.60 (s, 1H), 7.15 (s, 1H), 7.12 (d, J=2.0 Hz, 1H), 6.48 (d, J=2.0 Hz, 1H), 2.98~2.92 (m, 2H), 2.95 (s, 1H), 2.82~2.68 (m, 1H), 2.50~2.25 (m, 2H), 2.21~2.05 (m, 1H), 2.01~1.85 (m, 1H), 1.78~1.52 (m, 2H), 1.50~1.25 (m, 6H), 0.80 (s, 3H) MS (m/z) $MH^+$ (320).

EXAMPLE 12

Compound #9

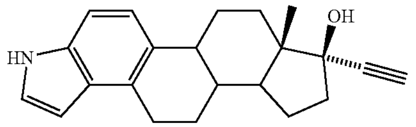

Lithium acetylide-ethylenedimine complex (69 mg, 0.784 mmol) was added into a mixture of Compound #2, prepared as in Example 4 (67 mg, 0.229 mmol) in dry dioxane (1 mL) and DMSO (1 mL) at room temperature. The reaction mixture was stirred for 1 h. The solvent was removed and then EtOAc and water were added. The mixture was partitioned between EtOAc and water. The organic layer was washed with water and brine, then dried over anhydrous $Na_2SO_4$, filtered and concentrated to yield the title compound as a crude yellow oil. The oil was purified by flash chromatography using 2:1 hexanes/EtOAc to yield the title compound as a yellowish oil.

$^1$H NMR (300 MHz, $CDCl_3$) δ 8.05 (br, s, 1H), 7.26 (s, 1), 7.20 (s, 1H), 7.15 (d, J=3.0 Hz, 1H), 6.48 (d, J=3.0 Hz, 1H), 3.10~2.95 (m, 2H), 2.60 (s, 1H), 2.52~2.25 (m, 4H), 2.10~1.85 (m, 2H), 1.80~1.65 (m, 2H), 1.55~1.32 (m, 5H), 0.88 (s, 3H) MS (m/z) $MH^+$ (320).

EXAMPLE 13

Compound #12

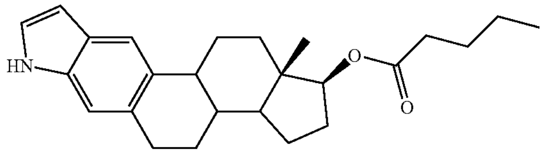

Pyridine (0.141 mmol, 12 μL) and catalytic amount of DMAP (1 mg) were added into in a mixture of 12a-methyl-1,2,3,3a,3b,4,5,7,10b,11,12,12a-dodecahydro-7-aza-dicylo-penta[a,h]phenanthren-1-ol, a known compound, (38 mg, 0.129 mmol) in $CH_2Cl_2$ (2 mL) at 0° C., followed by addition of valeric choride (0.129 mmol, 16 μL). The reaction mixture was stirred at 0° C. for 2 h and then warmed to room temperature. The mixture was partitioned between $CH_2Cl_2$ and water. The aqueous layer was extracted with $CH_2Cl_2$ twice. The combined organic layer was then washed with saturated $NH_4Cl$, water and brine, then dried over anhydrous $Na_2SO_4$, filtered and concentrated to yield the title compound as a crude solid. The solid was purified by flash chromatography using 3:1 hexanes/EtOAc to yield the title compound as a yellow solid.

$^1$H NMR (300 MHz, $CDCl_3$) δ 7.92 (br, s, 1H), 7.68 (s, 1H), 7.15 (s, 1H), 7.14 (s, 1H), 6.45 (s, 1H), 4.72 (t, J=8.5 Hz, 1H), 3.05 (m, 2H), 2.48~2.40 (m, 2h), 2.35 (t, J=7.5 Hz, 2H), 2.30~2.22 (m, 1H), 2.00~1.85 (d, J=9.5 Hz, 2H), 1.80~1.72 (m, 1H), 1.70~1.52 (m, 1H), 1.65 (t, J=7.5 Hz, 2H), 1.50~1.25 (m, 6H), 1.36 (m, J=7.5 Hz, 2H), 0.95 (t, J=7.5 Hz, 3H), 0.90 (s, 3H), MS (m/z) $MH^+$ (381).

EXAMPLE 14

Compound #11

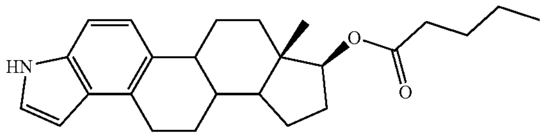

Pyridine (0.123 mmol, 10 μL) and catalytic amount of DMAP (1 mg) were added into in a mixture of 7a-methyl-3,5b,6,7,7a,8,9,10,10a,10b,11,12-dodecahydro-3-aza-dicyclopenta[a,l]phenanthren-8-ol, a known compound, (33 mg, 0.112 mmol) in $CH_2Cl_2$ (2 mL)at 0° C., followed by addition of valeryl choride (0.123 mmol, 27 μL). The reaction mixture was stirred at 0° C. for 2 h and then warmed to room temperature. The mixture was partitioned between $CH_2Cl_2$ and water. The aqueous layer was extracted with $CH_2Cl_2$ twice. The combined organic layer was then washed with saturated $NH_4Cl$, water and brine, then dried over anhydrous $Na_2SO_4$, filtered and concentrated to yield the title compound as a crude solid. The solid was purified by flash chromatography purification using 3:1 hexanes/EtOAc to yield the title compound as a yellow solid.

$^1H$ NMR (300 MHz, $CDCl_3$) δ 8.12 (s, br, 1H), 7.25 (d, J=3.0 Hz, 1H), 7.22 (d, J=3.0 Hz, 1H), 7.22 (d, J=3.0 Hz, 1H), 7.20 (d, J=3.5 Hz, 1H), 6.52 (d, J=3.0 Hz, 1H), 4.75 (t, J=8.5 Hz, 1H), 3.10~2.98 (m, 2H), 2.48~2.40 (m, 2H), 2.33 (t, J=8.0 Hz, 2H), 2.30~2.20 (m, 1H), 2.11~2.02 (m, 1H), 2.00~1.85 (m, 1H), 1.80~1.66 (m, 1H), 1.65 (t, J=8.0 Hz, 2H), 1.60~1.28 (m, 5H), 1.40 (m, J=8.0 Hz, 2H), 0.95 (t, J=8.5 Hz, 3H), 0.85 (s, 3H) MS (m/z) $MH^+$ (381).

EXAMPLE 15

Compound #13

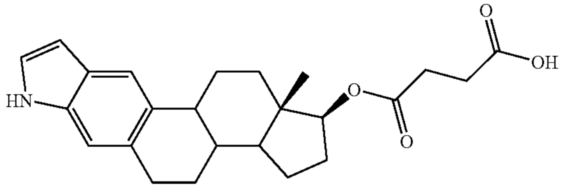

Pyridine (0.370 mmol, 30 μL) and catalytic amount of DMAP (10 mg) were added into in a mixture of 12a-methyl-1,2,3,3a,3b,4,5,7,10b,11,12,12a-dodecahydro-7-aza-dicylopenta[a,h]phenanthren-1-ol, a known compound, (68 mg, 0.231 mmol) in $CH_2Cl_2$ (2 mL) at 0° C., followed by addition of succinic anhydride (0.346 mmol, 35 mg). The reaction mixture was stirred at 0° C. for 2 h and at room temperature overnight. The mixture was then partitioned between $CH_2Cl_2$ and water. The aqueous layer was extracted with $CH_2Cl_2$ twice. The combined organic layer was then washed with saturated $NH_4Cl$, water and brine, then dried over anhydrous $Na_2SO_4$, filtered and concentrated to yield the title compound as a crude solid. The solid was purified by flash chromatography using 2:1 hexanes/EtOAc to yield the title compound as a yellow solid.

$^1H$ NMR (300 MHz, $CDCl_3$) δ 7.95 (br, s, 1H), 7.65 (s, 1H), 7.12 (s, 2H), 6.48 (s, 1H), 4.72 (t, J=7.0 Hz, 1H), 3.10 (m, 2H), 2.80~2.58 (m, 4H), 2.50~2.32 (m, 2H), 2.30~2.15 (m, 1H), 1.95~1.85 (d, J=9.0 Hz, 2H), 1.80 (m, 1H), 1.75~1.50 (m, 2H), 1.48~1.30 (m, 5H), 0.85 (s, 3H) MS (m/z) $MH^+$(396), $MH^-$ (394).

EXAMPLE 16

Compound #14

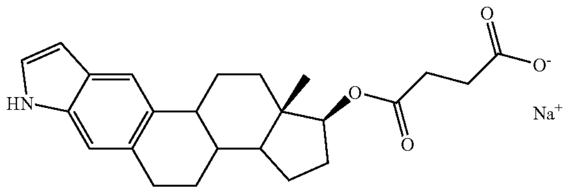

A solution of NaOH (0.0572 mmol, 1.0 N in THF solution) was added to Compound #13, prepared as in Example 15 (26 mg, 0.066 mmol). The mixture was stirred at room temperature for 1 h. The solvent was removed in vacuo to yield the title compound as a white solid. The solid was dried at 50° C. under vacuum for 10 h to yield the title compound as a white solid.

$^1H$ NMR (300 MHz, $CDCl_3$) δ 7.41 (s, 1H), 7.12 (d, J=3.0 Hz, 1H), 7.08 (s, 1H), 6.35 (d, J=3.0 Hz, 1H), 4.68 (t, J=8.5 Hz, 1H), 2.98 (m, 2H), 2.70~2.48 (m, 4H), 2.40~2.32 (m, 1H), 2.32~2.18 (m, 1H), 2.20~2.12 (m, 1H), 1.98~1.85 (m, 2H), 1.80~1.62 (m, 1H), 1.60~1.48 (m, 1H), 1.48~1.25 (m, 6H), 0.90 (s, 3H)

EXAMPLE 17

Compound #15

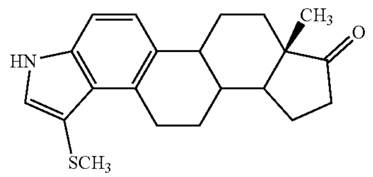

To a vigorously stirred solution of 3-Amino-13-methyl-6,7,8,9,11,12,13,14,15,16-decahydro-cyclopenta[a]phenanthren-17-one (101 mg, 0.37 mmoL) dichloromethane (5 mL) at −65° C. was added dropwise a soution of t-BuOCl (0.37 mmoL, 40 mg) in DCM (1 mL). After 5 min, 1,1-dimethoxy-2-methylsulfanyl-ethane (0.37 mmoL, 50 μL) dissolved in DCM (0.5 mL) was added to the reaction, followed by addition of $Et_3N$ (0.37 mmoL, 52 μL). The reaction mixture was then stirred for 1 h. To the reacted mixture was added DCM (10 mL), the resulting mixture was washed with 1N HCl, saturated $NaHCO_3$ and brine, then dried over anhydrous $Na_2SO_4$, filtered and concentrated to yield a crude product. The crude material was purified using column chromatography and a 3:1 hexanes:EtOAc mixture as eluent to yield the title compound as a pale solid.

$^1H$ NMR (300 MHz, $CDCl_3$) δ 8.10 (br, s, 1H), 7.20 (d, J=8.5 Hz, 1H), 7.15 (d, J=8.5 Hz, 1H), 6.52 (d, J=2.5 Hz, 1H), 3.25~3.01 (m, 2H), 2.65~2.38 (m, 3H), 2.50 (s, 3H), 2.25~1.90 (m, 4H), 1.82~1.48 (m, 6H), 0.92 (s, 3H) MS (m/z) $MH^+$ (340).

EXAMPLE 18

Estrogen Receptor α Flash Plate Assay

This assay monitors binding of radiolabeled estrogen to the estrogen receptor. It was performed on a BioMek 2000 (Beckman). Plates were read in a scintillation counter (Packard TopCount), with decreased counts an indication of binding of a compound to the receptor. The assay was run according to the procedure described by Allan, et al., *Anal. Biochem.* (1999), 275(2), 243–247.

On day one, 100 μL of Estrogen Screening Buffer (ESB, Panvera) containing 5 mM dithiothreitol (DTT, Panvera), 0.5 μg mouse anti-estrogen receptor monoclonal antibody (SRA-1010, Stressgen) and 50 ng purified human estrogen receptor α (nER-α, Panvera) were added to each well of a 96 well FlashPlate Plus plate crosslinked with goat anti-mouse antibodies (NEN Life Sciences). The plate was sealed and incubated at 4° C. overnight.

On day two, each well was washed three times with 200 μL PBS, pH 7.2, at room temperature. To each well was then added 98 μL radiolabeled estrogen (0.5 nM, which equals 6 nCi for a 120 Ci/mmol batch, Amersham), diluted in ESB and 5 mM dithiothreitol (DTT). To individual wells were then added 2.5 μL test compound diluted in 30% (v/v) dimethyl sulfoxide/50 mM HEPES, pH 7.5. The wells were mixed three times by aspiration, the plate sealed and incubated at room temperature for one hour. The wells were then counted for 1 min in a TopCount scintillation counter (Packard).

EXAMPLE 19

Estrogen Receptor β Fluorescence Polarization Assay

This assay monitors binding of a fluorescent analog of estrogen (Fluormone ES2, Panvera) to the estrogen receptor. Plates were read in a fluorometer that can be set to polarization mode. A decrease in fluorescence relative to vehicle control is an indication of binding of a compound to the receptor.

It is crucial to avoid introduction of air bubbles into the reaction in each well of the 96 well plate throughout this procedure. (Bubbles on the surface of the reaction disrupt light flow, affecting the polarization reading.) However, it is also crucial to effectively mix the reaction components upon addition to the well.

On ice, a 2× standard mixture of Assay Buffer (Panvera), 10 nM DTT and 40 nM ES2 was prepared. On ice, a 2× reaction mixture of Assay Buffer (Panvera), and 20 nM human estrogen receptor β (hER-β, Panvera) and 40 nM ES2 was also prepared.

Dilutions-of test compound were prepared in 30% (v/v) dimethyl sulfoxide/50 mM HEPES, pH 7.5. At this point, the dilutions were 40× the final required concentration.

The standard mixture at 50 μL was then added to each well. The reaction mixture at 48 μL was added to all wells. The compound dilution at 2.5 μL was added to the appropriate wells. The reaction mixtures were mixed using a manual pipette, a roll of aluminum foil adhesive cover was placed on the plate and the plate incubated at room temperature for 1 hour.

Each well on the plate was then read in an LjL Analyst with an excitation wavelength of 265 nm and an emission wavelength of 538.

Representative compound of the present invention were tested according to the procedure described above for binding to the Estrogen Receptor a and Estrogen Receptor β as described in Examples 18 and 19 above, with results as listed in Table 3.

TABLE 3

| ID No. | ERα Binding $IC_{50}$ (μM) | ERα at 1 μM % Inhibition | ERβ Binding $IC_{50}$ (μM) | ERβ at 1 μM % Inhibition |
|---|---|---|---|---|
| 1 | | 11 | | 6.2 |
| 2 | | 45 | | 27 |
| 3 | 2.2 | | >10 | |
| 4 | 1.4 | | 0.61 | |
| 6 | 0.042 | | 0.091 | |
| 7 | | 19 | | 14 |
| 8 | 0.040 | | 0.15 | |
| 12 | | 95 | | 96 |
| 13 | 0.92 | | 0.61 | |
| 15 | | 81 | | 66 |

EXAMPLE 20

MCF-7 Cell Proliferation Assay

This assay was run according to the procedure described by Welshons, et al., (*Breast Cancer Res. Treat.,* 1987, 10(2), 169–75), with minor modification.

Briefly, MCF-7 cells (from Dr. C. Jordan, Northwestern University) were maintained in RPMI 1640 phenol red free medium (Gibco) in 10% FBS (Hyclone), supplemented with bovine insulin and non-essential amino acid (Sigma). The cells were initially treated with 4-hydoxyltamoxifen ($10^{-8}$ M) and let stand at 37° C. for 24 hours. Following this incubation with tamoxifen, the cells were treated with compounds at various concentrations.

Compounds to be tested in the agonist mode were added to the culture media at varying concentrations. Compounds to be treated in the antagonist mode were prepared similarly, and 10 nM 17β-estradiol was also added to the culture media. The cells were incubated for 24 hours at 37° C. Following this incubation, 0.1 μCi of $^{14}C$-thymidine (56 mCi/mmol, Amersham) was added to the culture media and the cells were incubated for an additional 24 hours at 37° C. The cells were then washed twice with Hank's buffered salt solution (HBSS) (Gibco) and counted with a scintillation counter. The increase in the $^{14}C$-thymidine in the compound treated cells relative to the vehicle control cells were reported as percent increase in cell proliferation.

EXAMPLE 21

Alkaline Phosphatase Assay in Human Endometrial Ishikawa Cells

This assay was run according to the procedure described by Albert et a., *Cancer Res,* (9910), 50(11), 330-6-10, with minor modification.

Ishikawa cells (from ATCC) were maintained in DMEM/F12 (1:1) phenol red free medium (Gibco) supplemented with 10% calf serum (Hyclone). 24 hours prior to testing, the medium was changed to DMEM/F12 (1:1) phenol red free containing 2% calf serum.

Compounds to be tested in the agonist mode were added to the culture media at varying concentrations. Compounds to be treated in the antagonist mode were prepared similarly, and 10 nM 17β-estradiol was also added to the culture media. The cells were then incubated at 37° C. for 3 days. On the fourth day, the media was remove, 1 volume of 1× Dilution Buffer (Clontech) was added to the well followed by addition of 1 volume of Assay Buffer (Clontech). The cells were then incubated at room temperature for 5 minutes. 1 volume of freshly prepared Chemiluminescence Buffer (1 volume of chemiluminescent substrate (CSPD) in 19 volume Chemiluminescent Enhancer with final concentration of CSPD at 1.25 mM; Sigma Chemical Co.) was added. The cells were incubated at room temperature for 10 minutes and then quantified on a luminometer. The increase of chemiluminescence over vehicle control was used to calculate the increase in alkaline phosphatase activity.

Representative compound of the present invention were tested according to the procedure described in Examples 20 and 21 above, with results as listed in Table. 4.

TABLE 4

| ID No. | MCF7 (Breast) $EC_{50}$ (nM) | Ishikawa (Endometrial) $EC_{50}$ (nM) |
|---|---|---|
| 3 | 240 | 1.9 |
| 4 | 280 | 1.8 |
| 6 | 2.9 | 0.21 |
| 8 | 11 | 0.44 |
| 13 | 15 | 1.2 |

EXAMPLE 22

As a specific embodiment of an oral composition, 100 mg of the Compound #6, prepared as in Example 10 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations adaptations and/or modifications as come within the scope of the following claims and their equivalents.

What is claimed is:

1. A compound of formula (I)

(I)

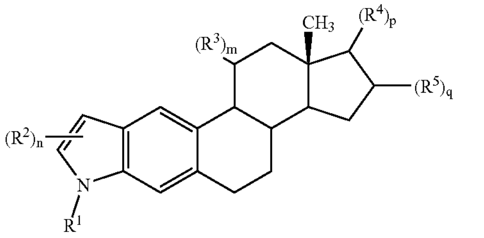

wherein $R^1$ is selected from the group consisting of hydrogen, hydroxy, A, —O-A, C(O)-A and —$SO_2$-A;

n is an integer from 0 to 2;

each $R^2$ is independently selected from the group consisting of hydroxy, carboxy, halogen, -A, —O-A, —C(O)-A, —C(O)O-A, amino, alkylamino, dialkylamino, cyano, aminocarbonyl, alkylaminocarbonyl, dialkylaminocarbonyl, —SH, —S-A, —SO-A, —$SO_2$-A, —$SO_2$—$NH_2$, —$SO_2$—NH(alkyl) and —$SO_2$—N$(alkyl)_2$;

m is an integer from 0 to 2;

each $R^3$ is independently selected from the group consisting of -A, —O-A, —S-A, —NH-A, —$N(A)_2$ and —C(O)-A;

p is an integer from 1 to 2;

each $R^4$ is independently selected from the group consisting of hydroxy, carboxy, cyano, -A, alkenyl, -alkenyl-A, alkynyl, -alkynyl-A, —O-A, —$NH_2$, NH(A), —$N(A)_2$, —N(A)-C(O)-A, —NH—C(O)-A, —C(O)—$N(A)_2$, —C(O)—$NH_2$, —C(O)—NH-A, —$SO_2$—$N(A)_2$, —$SO_2$—NH(A), —$SO_2$—$NH_2$, —N(A)-$SO_2$-A, —NH—$SO_2$-A, —C(O)O-A, —OC(O)H and —OC(O)-A;

alternatively, when p is 2, two $R^4$ groups may be taken together as oxo or =N(OH);

q is an integer from 0 to 2;

each $R^5$ is independently selected from the group consisting of hydroxy, carboxy, halogen, alkyl, alkoxy, cycloalkyl and —C(O)-A; wherein the alkyl group is optionally substituted with one or more substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one or more substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

2. A compound as in claim 1 wherein $R^1$ is selected from the group consisting of hydrogen, hydroxy, A, —O-A, C(O)-A and —$SO_2$-A;

n is an integer from 0 to 1;

each $R^2$ is independently selected from the group consisting of carboxy, halogen, -A, —C(O)-A, —C(O)O-A, cyano, —S-A, —SO-A, —$SO_2$-A, —$SO_2$—$NH_2$, —$SO_2$—NH(alkyl) and —$SO_2$—$N(alkyl)_2$;

m is an integer from 0 to 1;

each $R^3$ independently selected from the group consisting of -A, —O-A, —S-A, —NH-A and —C(O)-A;

p is an integer from 1 to 2;

$R^4$ is selected from the group consisting of hydroxy, —$NH_2$, —NH(A), —$N(A)_2$, —C(O)$NH_2$, —C(O)—NH(A), —$SO_2$—$NH_2$, —$SO_2$—NH(A) and —OC(O)-A, when the $R^4$ is in a β-orientation;

$R^4$ is selected from the group consisting of hydroxy, carboxy, cyano, -A, alkenyl, -alkenyl-A, alkynyl, -alkynyl-A, —O-A, —$NH_2$, —NH(A), —$N(A)_2$, —N(A)-C(O)-A, —NH—C(O)-A, —C(O)—$N(A)_2$, —C(O)—$NH_2$, —C(O)—NH-A, —$SO_2$—$N(A)_2$, —$SO_2$—NH(A), —$SO_2$—$NH_2$, —N(A)-$SO_2$-A, —NH—$SO_2$-A, —C(O)O-A, —OC(O)H and —OC(O)-A, when the $R^4$ in an α-orientation;

alternatively, when p is 2, two $R^4$ groups may be taken together as oxo or =N(OH);

q is an integer from 0 to 1;

$R^5$ is selected from the group consisting of carboxy, halogen, lower alkyl, and —C(O)-A; wherein the alkyl group is optionally substituted with one to two substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one to two substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

3. A compound as in claim 2 wherein $R^1$ is selected from the group consisting of hydrogen and —$SO_2$-alkyl;

n is 0;

m is 0;

p is an integer from 1 to 2;

$R^4$ is selected from the group consisting of hydroxy and —O—C(O)-alkyl; wherein the alkyl portion of the —O—C(O)-alkyl group is optionally substituted with a carboxy group;

alternatively when p is 2, two $R^4$ groups are taken together as oxo;

q is 0;

or a pharmaceutically acceptable salt thereof.

4. A compound as in claim 3 wherein $R^1$ is selected from the group consisting of hydrogen and —$SO_2$—$CH_3$;

n is 0;

m is 0;

p is an integer from 1 to 2;

$R^4$ is selected from the group consisting of hydroxy and —O—C(O)-n-butyl and —O—C(O)—$CH_2CH_2CH_2CH_2$—$CO_2H$;

alternatively when p is 2, two $R^4$ groups are taken together as oxo;

q is 0;

or a pharmaceutically acceptable salt thereof.

5. A compound of the formula (II)

(II)

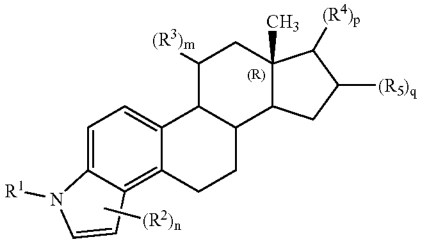

wherein $R^1$ is selected from the group consisting of hydrogen, hydroxy, A, —O-A, C(O)-A and —$SO_2$-A;

n is an integer from 0 to 2;

each $R^2$ is independently selected from the group consisting of hydroxy, carboxy, halogen, -A, —O-A, —C(O)-A, —C(O)O-A, amino, alkylamino, dialkylamino, cyano, aminocarbonyl, alkylaminocarbonyl, dialkylaminocarbonyl, —SH, —S-A, —SO-A, —$SO_2$-A, —$SO_2$—$NH_2$, —$SO_2$—NH(alkyl) and —$SO_2$—N$(alkyl)_2$;

m is an integer from 0 to 2;

each $R^3$ independently selected from the group consisting of -A, —O-A, —S-A, —NH-A, —$N(A)_2$ and —C(O)-A;

p is an integer from 1 to 2;

each $R^4$ is independently selected from the group consisting of hydroxy, carboxy, cyano, -A, alkenyl, -alkenyl-A, alkynyl, -alkynyl-A, —O-A, —$NH_2$, NH(A), —$N(A)_2$, —N(A)-C(O)-A, —NH—C(O)-A, —C(O)—$N(A)_2$, —C(O)—$NH_2$, —C(O)—NH-A, —$SO_2$—$N(A)_2$, —$SO_2$—NH(A), —$SO_2$—$NH_2$, —N(A)-$SO_2$-A, —NH—$SO_2$-A, —C(O)O-A, —OC(O)H and —OC(O)-A;

alternatively, when p is 2, two $R^4$ groups may be taken together as oxo or =N(OH);

q is an integer from 0 to 2;

each $R^5$ is independently selected from the group consisting of hydroxy, carboxy, halogen, alkyl, alkoxy, cycloalkyl and —C(O)-A; wherein the alkyl group is optionally substituted with one or more substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one or more substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

6. A compound as in claim 5 wherein $R^1$ is selected from the group consisting of hydrogen, hydroxy, A, —O-A, C(O)-A and —$SO_2$-A;

n is an integer from 0 to 1;

each $R^2$ is independently selected from the group consisting of carboxy, halogen, -A, —C(O)-A, —C(O)O-A, cyano, S-A —SO-A, —$SO_2$-A, —$SO_2$—$NH_2$, —$SO_2$—NH(alkyl) and —$SO_2$—$N(alkyl)_2$;

m is an integer from 0 to 1;

each $R^3$ independently selected from the group consisting of -A, —O-A, —S-A, —NH-A and —C(O)-A;

p is an integer from 1 to 2;

$R^4$ is selected from the group consisting of hydroxy, —$NH_2$, —NH(A), —$N(A)_2$, —C(O)$NH_2$, —C(O)—NH(A), —$SO_2$—$NH_2$, —$SO_2$—NH(A) and —OC(O)-A, when the $R^4$ in a β-orientation;

$R^4$ is selected from the group consisting of hydroxy, carboxy, cyano, -A, alkenyl, -alkenyl-A, alkynyl, -alkynyl-A, —O-A, —$NH_2$, —NH(A), —$N(A)_2$, —N(A)-C(O)-A, —NH—C(O)-A, —C(O)—$N(A)_2$, —C(O)—$NH_2$, —C(O)—NH-A, —$SO_2$—$N(A)_2$, —$SO_2$—NH(A), —$SO_2$—$NH_2$, —N(A)-$SO_2$-A, —NH—$SO_2$-A, —C(O)O-A, —OC(O)H and —OC(O)-A, when the $R^4$ is in an α-orientation;

alternatively, when p is 2, two $R^4$ groups may be taken together as oxo or =N(OH);

q is an integer from 0 to 1;

$R^5$ is selected from the group consisting of carboxy, halogen, lower alkyl, and —C(O)-A; wherein the alkyl group is optionally substituted with one to two substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one to two substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

7. A compound as in claim 6 wherein $R^1$ is selected from the group consisting of hydrogen and —$SO_2$-alkyl;

n is an integer from 0 to 1;

$R^2$ is selected from the group consisting of —S-(alkyl);

m is 0;

p is an integer from 1 to 2;

$R^4$ is selected from the group consisting of hydroxy, alkynyl and —O—C(O)-(alkyl);

alternatively, when p is 2, two $R^4$ groups are taken together as oxo;

q is 0;

or a pharmaceutically acceptable salt thereof.

8. A compound as in claim 7 wherein $R^1$ is selected from the group consisting of hydrogen and $—SO_2—CH_3$;

n is an integer from 0 to 1;

$R^2$ is $—S—CH_3$;

m is 0;

p is an integer from 1 to 2;

$R^4$ is selected from the group consisting of hydroxy, ethynyl and —OC(O)-n-butyl;

alternatively, when p is 2, two $R^4$ groups are taken together as oxo;

q is 0;

or a pharmaceutically acceptable salt thereof.

9. A pharmaceutical composition comprising a pharmaceutically acceptable carrier and a compound of claim 1.

10. A process for making a pharmaceutical composition comprising mixing a compound of claim 1 and a pharmaceutically acceptable carrier.

11. A method for treating a disorder mediated by an estrogen receptor, wherein the disorder is selected from the group consisting of osteoporosis, hot flashes, vaginal dryness, breast cancer and endometriosis.

12. A method of contraception comprising co-therapy with a therapeutically effective amount of a compound as in claim 1 and a progestogen or a progestogen antagonist.

13. A pharmaceutical composition comprising a pharmaceutically acceptable carrier and a compound of claim 5.

14. A process for making a pharmaceutical composition comprising mixing a compound of claim 5 and a pharmaceutically acceptable carrier.

15. A method for treating a disorder mediated by an estrogen receptor, wherein the disorder is selected from the group consisting of osteoporosis, hot flashes, vaginal dryness, breast cancer and endometriosis.

16. A method of contraception comprising co-therapy with a therapeutically effective amount of a compound as in claim 5 and a progestogen or a progestogen antagonist.

17. A method of contraception comprising co-therapy with a therapeutically effective amount of a compound of formula (II) and a progestogen or a progestogen antagonist, wherein formula (II) is as follows:

(II)

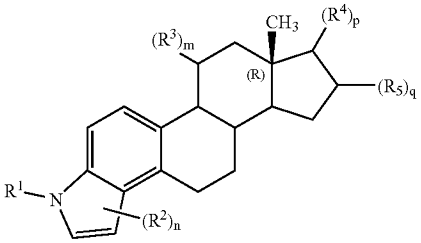

wherein $R^1$ is selected from the group consisting of hydrogen, hydroxy, A, —O-A, C(O)-A and $—SO_2$-A;

n is an integer from 0 to 2;

each $R^2$ is independently selected from the group consisting of hydroxy, carboxy, halogen, -A, —O-A, —C(O)-A, —C(O)O-A, amino, alkylamino, dialkylamino, cyano, aminocarbonyl, alkylaminocarbonyl, dialkylaminocarbonyl, —SH, —S-A, —SO-A, $—SO_2$-A, $—SO_2—NH_2$, $—SO_2$—NH(alkyl) and $—SO_2$—N(alkyl)2;

m is an integer from 0 to 2;

each $R^3$ is independently selected from the group consisting of -A, —O-A, —S-A, —NH-A, $—N(A)_2$ and —C(O)-A;

p is an integer from 1 to 2;

each $R^4$ is independently selected from the group consisting of hydroxy, carboxy, cyano, -A, alkenyl, -alkenyl-A, alkynyl, -alkynyl-A, —O-A, $—NH_2$, NH(A), $—N(A)_2$, —N(A)—CO-(A), —NH—C(O)-A, $—C(O)—N(A)_2$, $—C(O)—NH_2$, —C(O)—NH-A, $—SO_2—N(A)_2$, $—SO_2$—NH(A), $—SO_2—NH_2$, —N(A)-$SO_2$-A, —NH—$SO_2$-A, —C(O)O-A, —OC(O)H and —OC(O)-A;

alternatively, when p is 2, two $R^4$ groups may be taken together as oxo or =N(OH);

q is an integer from 0 to 2;

each $R^5$ is independently selected from the group consisting of hydroxy, carboxy, halogen, alkyl, alkoxy, cycloalkyl and —C(O)-A; wherein the alkyl group is optionally substituted with one or more substituents independently selected from halogen, hydroxy, carboxy or alkoxy;

wherein each A is independently selected from the group consisting of alkyl, aryl, aralkyl, cycloalkyl, heteroaryl and heterocycloalkyl; wherein the aryl, aralkyl, cycloalkyl, heteroaryl or heterocycloalkyl group is optionally substituted with one or more substituents independently selected from halogen, hydroxy, carboxy, lower alkyl, lower alkoxy, nitro, cyano, amino, lower alkylamino or di(lower alkyl)amino;

or a pharmaceutically acceptable salt thereof.

* * * * *